(12) United States Patent
Navawongse et al.

(10) Patent No.: US 11,376,594 B2
(45) Date of Patent: Jul. 5, 2022

(54) APPARATUS AND SYSTEM FOR BIOFLUID SAMPLE DISPENSING AND/OR ASSAY

(71) Applicant: Nitto Denko Corporation, Osaka (JP)

(72) Inventors: Rapeechai Navawongse, Singapore (SG); Ying Song Wang, Singapore (SG); Visit Thaveeprungsriporn, Singapore (SG); Yuen Hsia Cheng, Singapore (SG); Charm Nyein Lynn, Singapore (SG); Roland Galang Pulido, Singapore (SG); Feng Liu, Singapore (SG)

(73) Assignee: Nitto Denko Corporation

( * ) Notice: Subject to any disclaimer, the term of this patent is extended or adjusted under 35 U.S.C. 154(b) by 1007 days.

(21) Appl. No.: 15/772,758

(22) PCT Filed: Nov. 4, 2016

(86) PCT No.: PCT/SG2016/050547
§ 371 (c)(1),
(2) Date: May 1, 2018

(87) PCT Pub. No.: WO2017/078630
PCT Pub. Date: May 11, 2017

(65) Prior Publication Data
US 2019/0224680 A1    Jul. 25, 2019

Related U.S. Application Data

(60) Provisional application No. 62/250,573, filed on Nov. 4, 2015.

(51) Int. Cl.
*B01L 3/00* (2006.01)
*G01N 35/10* (2006.01)
(Continued)

(52) U.S. Cl.
CPC ......... *B01L 3/502776* (2013.01); *B01L 3/502* (2013.01); *B01L 3/50273* (2013.01);
(Continued)

(58) Field of Classification Search
None
See application file for complete search history.

(56) References Cited

U.S. PATENT DOCUMENTS 5,368,820 A * 11/1994 Lautenschlager ...... B01J 19/126
220/203.11
5,408,326 A   4/1995 Wang
(Continued)

FOREIGN PATENT DOCUMENTS

CN    103756867 A    4/2014
CN    104412075 A    3/2015
(Continued)

OTHER PUBLICATIONS

International Search Report for Application PCT/SG2016/050547 dated Feb. 1, 2017.
(Continued)

*Primary Examiner* — Brian R Gordon
(74) *Attorney, Agent, or Firm* — Lerner, David, Littenberg, Krumholz & Mentlik, LLP

(57) ABSTRACT

A system for assaying biofluid samples including an assay apparatus and a dispensing apparatus. The dispensing apparatus includes cuvettes that contain reagents and the biofluid samples to form assay samples, and the assay apparatus has a receptable for receiving and sealing the cuvettes inside. Once the cuvettes are sealed in the receptable, the assay apparatus performs assay processes on the assay samples in the cuvettes.

10 Claims, 20 Drawing Sheets

(51) Int. Cl.
*G01N 33/554* (2006.01)
*G01N 33/50* (2006.01)
*G01N 35/00* (2006.01)
*C12Q 1/25* (2006.01)
*G01N 35/04* (2006.01)

(52) U.S. Cl.
CPC .......... *B01L 3/502715* (2013.01); *C12Q 1/25* (2013.01); *G01N 33/50* (2013.01); *G01N 33/554* (2013.01); *G01N 35/00* (2013.01); *G01N 35/10* (2013.01); *B01L 2200/0605* (2013.01); *B01L 2300/048* (2013.01); *B01L 2300/0832* (2013.01); *B01L 2300/0867* (2013.01); *B01L 2400/0457* (2013.01); *B01L 2400/0478* (2013.01); *B01L 2400/0633* (2013.01); *G01N 2035/0436* (2013.01)

(56) References Cited

U.S. PATENT DOCUMENTS

| | | | | |
|---|---|---|---|---|
| 5,700,429 | A * | 12/1997 | Buhler | B01L 9/06 422/560 |
| 6,036,923 | A * | 3/2000 | Lagharn, Jr. | B01J 3/00 422/502 |
| 6,315,902 | B1 * | 11/2001 | Collasius | B01L 3/5025 210/232 |
| 6,361,746 | B1 * | 3/2002 | Wlodarski | B01L 7/00 200/500 |
| 6,455,005 | B1 * | 9/2002 | Berray | B01L 3/50853 215/247 |
| 6,511,634 | B1 * | 1/2003 | Bradshaw | B01F 13/002 206/268 |
| 6,610,252 | B2 * | 8/2003 | Madril | F26B 5/06 422/501 |
| 7,000,785 | B2 * | 2/2006 | Jafari | B01L 9/06 211/60.1 |
| 7,922,986 | B2 * | 4/2011 | Byrnard | G01N 35/026 422/561 |
| 7,939,036 | B2 * | 5/2011 | Burkhardt | G01N 21/253 422/561 |
| 8,404,489 | B2 * | 3/2013 | Akashi | B01L 3/502 436/94 |
| 8,440,151 | B2 * | 5/2013 | Voit | B01L 3/50853 422/559 |
| 8,900,533 | B2 * | 12/2014 | Cohen | B01L 9/543 422/564 |
| 2003/0215957 | A1 | 11/2003 | Lemmo et al. | |
| 2004/0033168 | A1 * | 2/2004 | Hughes | B01L 3/5025 422/561 |
| 2005/0042768 | A1 * | 2/2005 | Fredrick | B82Y 30/00 506/33 |
| 2008/0182301 | A1 | 7/2008 | Handique et al. | |
| 2010/0252116 | A1 | 10/2010 | Kilcoin et al. | |
| 2011/0182784 | A1 * | 7/2011 | Suzuki | B01L 9/06 422/561 |
| 2012/0293796 | A1 | 11/2012 | Ludowise et al. | |
| 2013/0078736 | A1 * | 3/2013 | Grover | B01L 3/0217 436/180 |
| 2013/0315780 | A1 | 11/2013 | Cook et al. | |
| 2015/0050186 | A1 | 2/2015 | Bammesberger et al. | |
| 2015/0132841 | A1 * | 5/2015 | Sampson | B01L 9/06 435/306.1 |
| 2015/0132860 | A1 | 5/2015 | Cook et al. | |
| 2015/0140669 | A1 | 5/2015 | Boehm et al. | |
| 2015/0160119 | A1 | 6/2015 | Marshall et al. | |
| 2015/0298120 | A1 | 10/2015 | Westberg et al. | |
| 2015/0346105 | A1 | 12/2015 | Gutsell et al. | |

FOREIGN PATENT DOCUMENTS

| | | |
|---|---|---|
| EP | 0096360 A1 | 12/1983 |
| EP | 2662137 A1 | 11/2013 |
| EP | 2662139 A1 | 11/2013 |
| GB | 2516672 A | 2/2015 |
| JP | 2000500331 A | 1/2000 |
| JP | 2008149221 A | 7/2008 |
| JP | 2012522996 A | 9/2012 |
| JP | 2015516084 A | 6/2015 |
| JP | 2015516583 A | 6/2015 |
| JP | 2016506238 A | 3/2016 |
| WO | 9716561 A1 | 5/1997 |
| WO | 0025924 A1 | 5/2000 |
| WO | 2011006671 A1 | 1/2011 |
| WO | 2014087149 A2 | 6/2014 |
| WO | 2015088942 A1 | 6/2015 |
| WO | 2015130225 A1 | 9/2015 |
| WO | 2015130233 A1 | 9/2015 |

OTHER PUBLICATIONS

Extended European Search Report including Written Opinion for EP16862577.0 dated May 13, 2019.
Search Report from First Office Action for Chinese Application No. 2016800779535 dated Apr. 30, 2021; 2 pages.
Search Report from First Office Action for Indian Application No. 201827020717 dated Mar. 12, 2021; 2 pages.

* cited by examiner

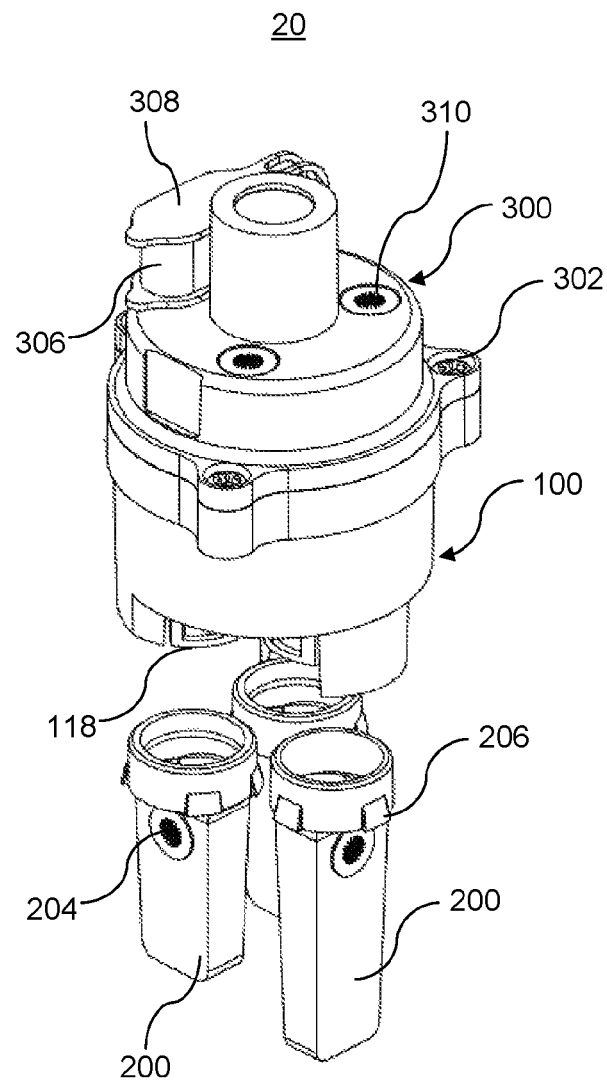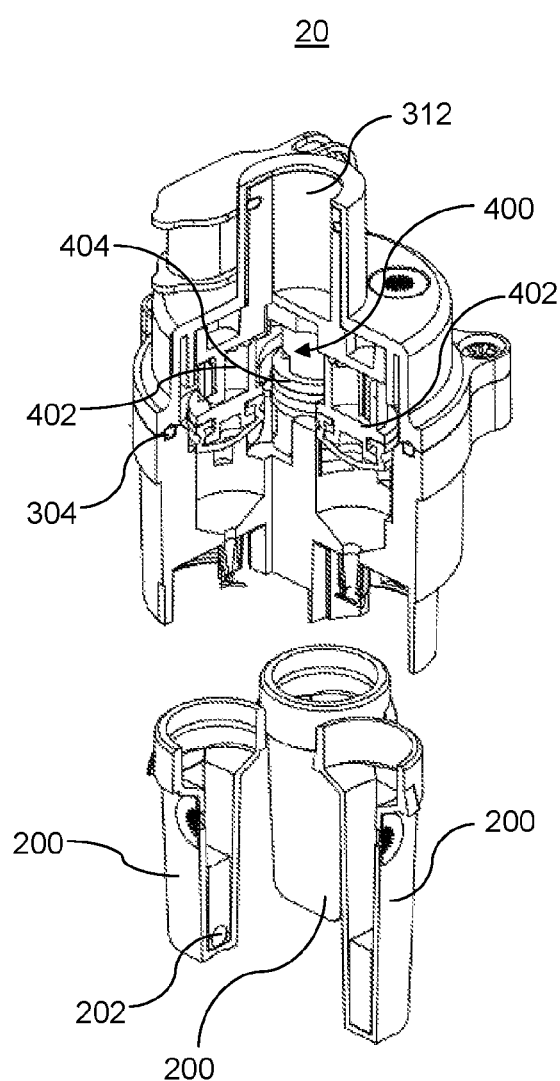
FIG. 3A
FIG. 3B

APPARATUS AND SYSTEM FOR BIOFLUID SAMPLE DISPENSING AND/OR ASSAY

CROSS REFERENCE TO RELATED APPLICATIONS

The present application is a national phase entry under 35 U.S.C. § 371 of International Application No. PCT/SG2016/050547 filed on Nov. 4, 2016, which claims priority from U.S. Patent Application No. 62/250,573 filed on Nov. 4, 2015, all of which are hereby incorporated herein by reference.

TECHNICAL FIELD

The present disclosure generally relates to an apparatus or apparatuses and a system or systems for collecting, metering, dispensing and/or assaying at least one biological fluid (biofluid). More particularly, the present disclosure describes various embodiments of an apparatus and a system for collecting, metering, and dispensing samples of at least one biofluid, e.g. bio-organic fluids produced by organisms, and assaying the biofluid samples, e.g. with reagents.

BACKGROUND

In broad terms, an assay is an investigative or analytic procedure in medicine and/or biology contexts for qualitatively assessing or quantitatively measuring the presence or amount or the functional activity of analytes in biofluid samples. Depending on the type of biofluid in the samples, assays may be used to detect the presence or extent of a disease in a subject. The biofluid may be excreted or secreted from the organisms (e.g. living persons) and may include, but are not limited to, serum, plasma, urine, blood, saliva, interstitial fluid, and cytosol.

For example, urinalysis is a type of assay performed on biofluid samples from living persons that provides a source of information about the anatomy and function of the person's kidneys and urinary tract. It provides insights into the status of systemic diseases such as chronic kidney disease and/or diabetes mellitus. Test strips, or dipsticks, for urinalysis are widely used for health screening purposes because they provide a simple protocol and are cost-effective. Although dipstick urinalysis is convenient, false positive and false negative results can occur due to colour change discrimination when performed by a human eye (e.g. by a nurse). It is known that degradation of colour occurs over time for dipstick urinalysis thus, results yielded may defer from the actual result. Currently, most point-of-care devices available in the market for urinalysis are only semi-quantitative and use a test strip and strip reader.

A fully quantitative urinalysis result can be obtained using an automatic urine analyzer at a hospital or a clinical laboratory. However, a urine analyzer is generally a large desktop machine or part of a larger piece of equipment, such as a fully automated blood serum/urine analyzer whereby a precision pipette system being a sub-system within the main system for dispensing a precise sample volume. These automated analyzers are expensive and require large spaces and trained personnel. They may be unsuitable if there is low volume, and also unsuitable for point-of-care testing. Therefore, these analyzers are located at centralized locations, and people who live in rural areas have limited access to proper diagnostic tests.

In an example of a urinalysis assay process, concurrent analysis of multiple substances may be useful for a more accurate diagnosis. As described in PCT publication WO 2015/130225, Chronic Kidney Disease (CKD) can be diagnosed in its early stages by measuring microalbuminuria in urine. WO 2015/130225 also describes tests for diagnosing CKD, such as by determining urine microalbuminuria and creatinine concentrations and the corresponding albumin-to-creatinine ratio (ACR). While the tests may be used to analyze a urine sample, the tests are also suitable for analyzing other biofluid samples (e.g. saliva, blood, etc.). As such, the term "urine microalbuminuria" or "microalbuminuria" may be more broadly referred to as "albumin".

Microalbuminuria/albumin and creatinine concentrations are separately measured from urine and the ACR of the urine is then calculated. In order to calculate ACR, two albumin and one creatinine reagents are used for their measurements, respectively. The reagents may be wet, e.g. in liquid or aqueous form, or dry, e.g. in powder form. A first reagent—bromocresol green (BCG)—is used for albumin detection, and a second reagent—3,5-dinitrobenzoic acid (DNBA) or alternatively picric acid—is used for creatinine detection. ACR is a useful parameter for diagnosing CKD or more generally as a prognosis factor for kidney failure risk.

Albumin and creatinine concentrations can be measured at different times or in different steps, however this takes a longer time and needs more manual operation steps, so concurrent analysis is desirable to reduce measurement time. However, manual operation steps are prone to human errors that contribute to inconsistent, less reliable results. Measurement of albumin and creatinine may require chemical reactions of urine with reagents and a suitable reaction time is required to obtain accurate and consistent results. Manual operation steps may result in measuring for albumin and creatinine too early or too late, i.e. the reaction time is inconsistent or incorrect.

Trained personnel and supporting lab equipment may be required for improving the urinalysis assay process. For example, to improve repeatability, precision, and accuracy for measuring and dispensing biofluid samples, precision pipettes and sophisticated dispensing systems like syringe pumps are used. However, these equipments may not suitable to be integrated into a point-of-care device for home or clinical use, due to their spatial footprint and cost.

Therefore, in order to address or alleviate at least one of the aforementioned problems and/or disadvantages, there is a need to provide an apparatus and a system for dispensing and/or assaying at least one biofluid, in which there is at least one improvement and/or advantage over the aforementioned prior art.

SUMMARY

According to a first aspect of the present disclosure, there is an apparatus for dispensing biofluid samples (i.e. a biofluid sample dispensing apparatus). The apparatus comprises a cartridge comprising a set of reservoirs and a set of cavities, each cavity residing within a reservoir and configured for dispensing a predetermined sample volume of biofluid. Each reservoir comprises: an inlet for receiving the biofluid; an outlet in fluid communication with the inlet; a peripheral barrier surrounding the outlet for containing the biofluid sample within a cavity residing within said reservoir and preventing fluid communication with another cavity; a valve disposed at the outlet for releasably sealing the biofluid sample within the cavity; and an overflow outlet configured to limit the predetermined volume of the biofluid sample which is containable within the cavity and which is dispensable from the cavity through the valve.

According to a second aspect of the present disclosure, there is an apparatus for assaying biofluid (i.e. a biofluid assaying apparatus). The apparatus comprises: a receptacle for housing a set of cuvettes of a biofluid sample dispensing apparatus, each cuvette being configured for containing an assay sample comprising a reagent and a sample of the biofluid; a receptacle sealing element for providing sealing engagement between the receptacle and the biofluid sample dispensing apparatus for sealing the cuvettes within the receptacle; and an automated system connected to the receptacle for performing an assay process on the assay samples in the cuvettes, while maintaining the cuvettes within the receptacle.

According to a third aspect of the present disclosure, there is a system for dispensing and assaying biofluid. The system comprises a biofluid sample dispensing apparatus and a biofluid assay apparatus. The biofluid sample dispensing apparatus comprises a set of reservoirs; a set of cavities, each cavity residing within a reservoir and configured for dispensing a predetermined sample volume of biofluid; a set of valves for releasably sealing the biofluid samples in the cavities, each valve being coupled to a cavity; and a set of cuvettes for receiving the biofluid samples through the valves, each cuvette being coupleable to at least one cavity and containing a reagent. The biofluid assay apparatus comprises: a receptacle for housing the cuvettes; a receptacle sealing element for providing sealing engagement between the receptacle and the biofluid sample dispensing apparatus for sealing the cuvettes within the receptacle; and an automated system connected to the receptacle for performing an assay process on an assay sample in each cuvette.

According to a fourth aspect of the present disclosure, there is an apparatus for dispensing biofluid samples (i.e. a biofluid sample dispensing apparatus). The apparatus comprises a cartridge comprising a plurality of reservoirs and a plurality of cavities, each cavity residing within a reservoir, the cartridge configured for self-apportioning a bulk sample of biofluid into a plurality of samples of biofluid containable within the cavities. Each reservoir comprises: an inlet for receiving the biofluid; an outlet in fluid communication with the inlet; a peripheral barrier surrounding the outlet for containing a predetermined volume of the biofluid sample within a cavity residing within said reservoir and permitting fluid communication with another cavity for volumes above the predetermined volume; and a valve disposed at the outlet for releasably sealing the biofluid sample within the cavity.

An advantage of one or more of the above aspects of the present disclosure is that the apparatuses and/or system can provide a more cost-effective solution for metering, dispensing, and assaying biofluid samples with reagents. The apparatuses and/or system are also more compact with a smaller spatial footprint. As such, they are more portable and would be suitable as an in vitro diagnostic (IVD) device and as a quantitative point-of-care device for home or clinical use. The portability factor enables decentralised or bed-side quantitative measurements, allowing users to perform self-diagnosis at home without going to the clinics or hospitals.

Another advantage is that several common and manual processes such as metering and dispensing of the biofluid samples, as well as the performance of one or more assay processes are more automatic and/or occur naturally as a result of the apparatus design. Non-skilled personnel, e.g. home users, would be able to perform the assay processes with greater reliability and repeatability, and the assay results obtained would be more consistent and less prone to human errors.

Yet another advantage is that multiple biofluid samples can be obtained at the same time, giving more convenience to home users to load a bulk sample of a biofluid into the cartridge only once and obtain multiple biofluid samples for performing the assay processes. Moreover, the biofluid samples may be dispensed into the cuvettes at the same time, such that the biofluid samples can react with the reagents in the cuvettes at the same time. Assay processes can also thus be performed on the assay samples substantially simultaneously. This improves the efficiency of the assay processes as multiple assay measurements and results can be obtained at substantially the same time.

An apparatus and a system for dispensing and/or assaying at least one biofluid according to the present disclosure are thus disclosed herein. Various features, aspects, and advantages of the present disclosure will become more apparent from the following detailed description of the embodiments of the present disclosure, by way of non-limiting examples only, along with the accompanying drawings.

BRIEF DESCRIPTION OF THE DRAWINGS

FIG. 3A illustrates a perspective view of an apparatus for dispensing biofluid samples, in accordance with an embodiment of the present disclosure.

FIG. 3B illustrates a cross-sectional perspective view of the apparatus of FIG. 3A, in accordance with an embodiment of the present disclosure.

DETAILED DESCRIPTION

In the present disclosure, depiction of a given element or consideration or use of a particular element number in a particular figure or a reference thereto in corresponding descriptive material can encompass the same, an equivalent, or an analogous element or element number identified in another figure or descriptive material associated therewith. The use of "/" in a figure or associated text is understood to mean "and/or" unless otherwise indicated. As used herein, the term "set" corresponds to or is defined as a non-empty finite organization of elements that mathematically exhibits a cardinality of at least one (e.g. a set as defined herein can correspond to a unit, singlet, or single element set, or a multiple element set), in accordance with known mathematical definitions. The recitation of a particular numerical value or value range herein is understood to include or be a recitation of an approximate numerical value or value range.

For purposes of brevity and clarity, descriptions of embodiments of the present disclosure are directed to an apparatus and a system for dispensing and/or assaying at least one biofluid, in accordance with the drawings. While aspects of the present disclosure will be described in conjunction with the embodiments provided herein, it will be understood that they are not intended to limit the present disclosure to these embodiments. On the contrary, the present disclosure is intended to cover alternatives, modifications and equivalents to the embodiments described herein, which are included within the scope of the present disclosure as defined by the appended claims. Furthermore, in the following detailed description, specific details are set forth in order to provide a thorough understanding of the present disclosure. However, it will be recognized by an individual having ordinary skill in the art, i.e. a skilled person, that the present disclosure may be practiced without specific details, and/or with multiple details arising from combinations of aspects of particular embodiments. In a number of instances, well-known systems, methods, procedures, and components have not been described in detail so as to not unnecessarily obscure aspects of the embodiments of the present disclosure.

Biofluid Sample Dispensing Apparatus 20

Figure 1:
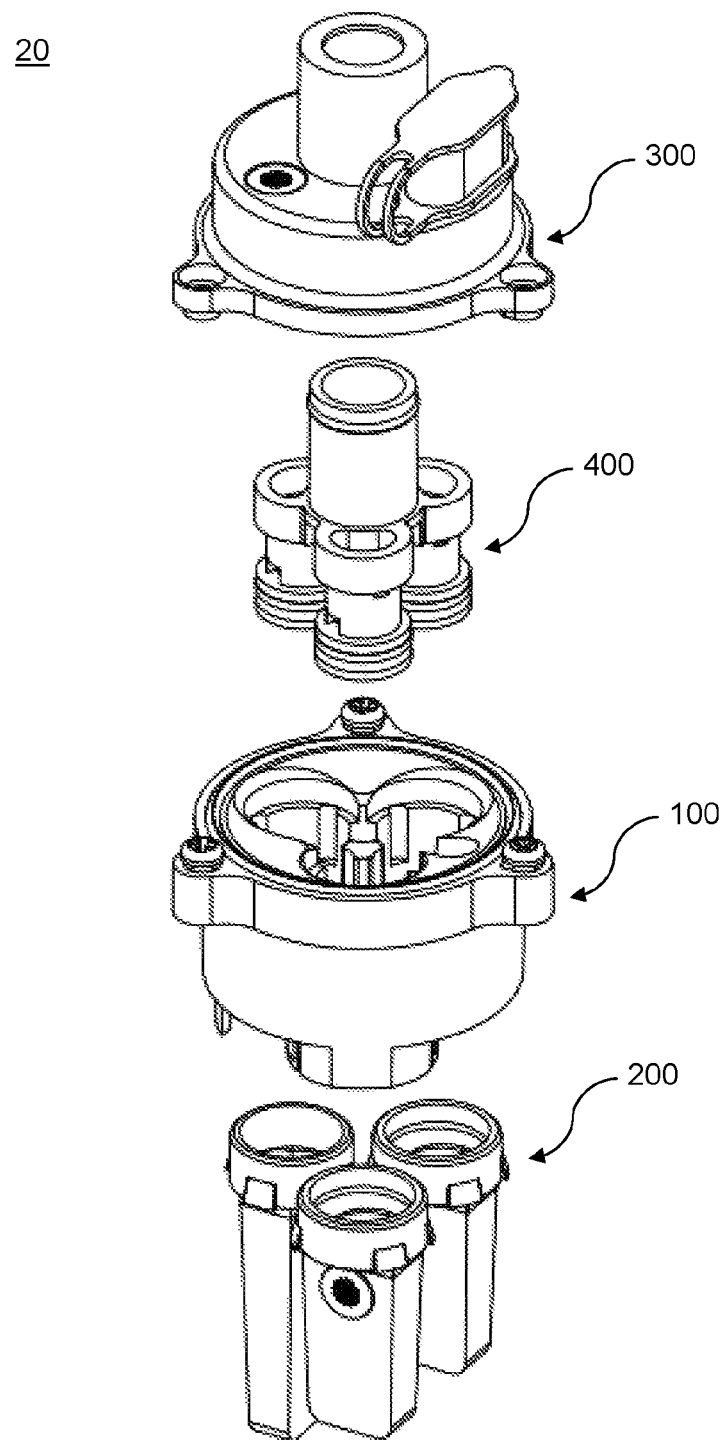
FIG. 1 illustrates an exploded view of an apparatus for dispensing biofluid samples, in accordance with an embodiment of the present disclosure.

In representative or exemplary embodiments of the present disclosure, there is an apparatus 20 for dispensing samples of at least one biofluid, i.e. a biofluid sample dispensing apparatus 20 as illustrated in FIG. 1. The at least one biofluid may comprise a bulk sample of biofluid such as urine excreted from a living person for diagnosing kidney-related diseases or CKD. The biofluid sample dispensing apparatus 20 comprises a cartridge 100 for holding and/or metering smaller test samples of the bulk sample of biofluid, a set of cuvettes 200 for receiving the biofluid samples from the cartridge 100, a cover 300 for covering the cartridge 100, and a piston assembly 400 for releasing or dispensing the biofluid samples from the cartridge 100 into the cuvettes 200.

Various components of the apparatus 20 may be fabricated by moulding or other known manufacturing methods. The components may be made of any of, but not limited to, the following materials—polypropylene/polypropene (PP), high-density polyethylene (HDPE), silicone, butyl rubber, nitrate rubber, and poly(methyl methacrylate) (PMMA), or a combination of materials—styrene acrylonitrile resin (SAN). The material PMMA may alternatively be known as acrylic or acrylic glass, as well as by the trade names Plexigas®, Acrylite®, Lucite®, and Perspex®. Where appropriate, various components of the apparatus 20 are assembled together with sealing elements to prevent or at least mitigate leakage of biofluid. Such sealing elements may include, but are not limited to, O-rings or gaskets made of resilient materials, rubber/silicon tight fitting connections, ultraviolet bonding, ultrasonic bonding, adhesive glue, latching, cantilever, etc.

Cartridge 100

With reference to FIG. 2A to FIG. 2D, the cartridge 100 comprises a set of cavities 102 and a set of reservoirs 103. More particularly, the cartridge 100 comprises a plurality of cavities 102 configured for self-apportioning the bulk sample of biofluid into a plurality of samples of biofluid. Each cavity 102 resides within a respective reservoir 103 of the cartridge 100 and is configured for containing a sample of the biofliud, i.e. a part or portion of the bulk sample of biofluid for subsequent assays. Each cavity 102 is further configured for dispensing a predetermined sample volume of biofluid for the subsequent assays. The bulk sample of the biofluid is apportioned to the cavities 102, such that each cavity 102 receives some biofluid, by fluid transfer across connecting spaces 105 located between the reservoirs 103.

Each reservoir 103 comprises an inlet 104 and an outlet 106 which are in fluid communication. In various embodiments, the inlet 104 is positioned above the outlet 106 for receiving the biofluid, and such that biofluid can communicate or flow from the inlet 104 to the outlet 106 by gravity. Each reservoir 103 further comprises a peripheral barrier 108 surrounding the outlet 106 and provides a wall or weir where the reservoirs 103 connect. Notably, the spaces 105 are formed on the peripheral barriers 108. The peripheral barrier 108 may be tapered or have a gradient to assist fluid flow from the inlet 104 to the outlet 106. The peripheral barrier 108, specifically the space 105 thereof, may permit fluid communication of each reservoir 103 with one or more other reservoirs 103/cavities 102 for volumes of the biofluid sample above the predetermined volume, i.e. for excess amounts of the biofluid sample beyond the predetermined volume in the cavities 102. Accordingly, the reservoirs 103 may be fluidly communicable with one another through the spaces 105.

Each cavity 102 shares with the respective reservoir 103 the outlet 106 such that the cavity 102 is able to dispense the biofluid sample through the outlet 106. Each cavity 102 comprises a valve 110 disposed at the outlet 106, specifically below the outlet 106, for releasably sealing the biofluid sample within the cavity 102. The valve 110 may be integrated with, or attached/inserted to the outlet 106. The valve 110 regulates, directs, or controls the flow of a fluid by opening, closing, or partially obstructing passageway(s) in the valve 110. Specifically, the valve 110 is configured to switch or move between a closed state (default state) and an open state depending on the fluid flow through the valve 110 or fluid flow rate. For example, when the cavity 102 is holding the biofluid sample without any external force, pressure, or weight acting on the biofluid sample, the valve 110 remains in the default closed state. The cavity 102, together with the valve 110 in the closed state, seals/holds/contains the biofluid sample. Upon application of an external force, such as by the piston assembly 400 to dispense the biofluid sample out from the cavity 102, the biofluid sample becomes pressurized and forces the valve 110 to change from the closed state to the open state. The valve 110 in the open state enables the biofluid sample to be released or dispensed from the outlet 106 of the cavity 102. The valve 110 in the open state may allow fluid communication through the outlet 106 at one side of the outlet 106. The valve 110 may be in the form or configuration of a duckbill valve which is commonly used in medical applications to prevent contamination due to backflow. Other forms or configurations of the valve 110 or valve types to perform the same or similar functions would be readily apparent to the skilled person.

Each reservoir 103 further comprises an overflow outlet 112 configured to limit the predetermined volume of the biofluid sample which is containable within the cavity 102. Accordingly, each overflow outlet 112 is configured for metering a precise volume of the biofluid sample in the respective cavity 102. The particular amount of the biofluid sample contained within each cavity 102 is the metered volume for subsequent dispensation through the valve 110. Preferably, the biofluid samples contained within each cavity 102 are dispensable through the valves 110 at substantially the same time.

In some embodiments, the overflow outlet 112 may be a cut-out portion or channel formed on the peripheral barrier 108. The overflow outlet 112 may comprise an upper or first overflow outlet plane 112A and a lower or second overflow outlet plane 112B. Further, the overflow outlet 112 may be configured to be co-planar with the space 105 also having an upper or first space plane 105A and a lower of second space plane 105B. More specifically, the first overflow outlet plane 112A may be co-planar with the first space plane 105A, and the second overflow outlet plane 112B may be co-planar with the second space plane 105B. Alternatively, the spacing between the planes 112A and 112B, and between the planes 105A and 105B may be different or varied to account for different volumes of the biofluid samples.

The overflow outlet 112 directs fluid away from the reservoir 103. Particularly, when the biofluid sample contained within the cavity 102 exceeds the predetermined volume or goes above the overflow outlet 112, specifically the level of the second overflow outlet plane 112B, excess amounts of the biofluid sample are channelled away from the cavity 102. The overflow outlet 112 is positioned at a height above the outlet 106, and limits or meters the amount of the biofluid sample to be contained in the cavity 102. Amounts or volumes of the biofluid sample above the predetermined volume, i.e. above the level indicated by the lower plane 112B of the overflow outlet 112, are discharged from the overflow outlet 112. In some other embodiments, the overflow outlet 112 may be or refer to the brim region of the cavity 102. Particularly, when the biofluid sample is introduced into the cavity 102 from the inlet 104, the cavity 102 would be filled. Any excess volumes introduced into the cavity 102 would overflow from the overflow outlet 112 over the peripheral barrier 108.

The overflow outlet 112 may be sized or shaped accordingly in conjunction with the peripheral barrier 108 configured to hold or retain the precise predetermined volume of the biofluid sample in the respective cavity 102. More specifically, the overflow outlet 112 may be semi-circularly elongated formed as a recess or protrusion. Alternatively, each respective cavity 102 may be sized in different volumes configured to dispense a variable precise predetermined volume of the biofluid sample for the subsequent assays. Yet alternatively, the overflow outlet 112 may be a channel with an entry hole located at a predefined height with respect to the peripheral barrier 108 for receiving and transferring excess biofluid sample away from the respective reservoir 103.

The cartridge 100 comprises a number of cavities 102, i.e. one or more, such as three cavities 102 as shown in the drawings. The cartridge 100 may thus be a single-cavity cartridge 100 or a multi-cavity cartridge 100 and the same working principle applies analogously. The number of cavities 102 is equal to the number of assays to be performed on the biofluid samples contained within the cavities 102. The cavities 102, and correspondingly the reservoirs 103, may be circumferentially arranged around a central vertical axis of the cartridge 100. More specifically, the cavities 102 and reservoirs 103 may be equiangularly spaced apart relative to the central vertical axis. In some other embodiments, the arrangement of the cavities 102 and reservoirs 103 may be different, such as with different angles between them. Alternatively, the cavities 102 and reservoirs 103 may be arranged in an array or grid-like form.

The cartridge 100 comprises a loading channel 114 for guiding or directing the flow of the bulk sample of biofluid into the reservoirs 103 and towards the cavities 102. Alternatively, the cartridge 100 comprises a set of loading channels 114 spaced apart from one another for guiding or directing the flow of the bulk sample of biofluid into each reservoir 103 and towards each cavity 102. Each of the loading channels 114 may be sloped with a predefined gradient or angle to further enhance gravitational effect for flow of the bulk sample of biofluid. Each cavity 102 thus receives a smaller or test sample of the bulk sample of biofluid loaded by the user. The overflow outlet 112 for each reservoir 103 limits the predetermined volume of the biofluid sample in the cavity 102 by allowing excess volumes above the predetermined volume to be discharged. The overflow outlets 112 may be horizontally planar to one another, and/or the outlets 106 may be horizontally planar to one another, such that each cavity 102 can contain identical volumes of the biofluid samples. Alternatively, one or more overflow outlets 112 and/or one or more outlets 106 may be at a different horizontal level to vary the predetermined volumes in one or more cavities 102.

In some embodiments as shown in FIG. 2A to FIG. 2D, the cartridge comprises three cavities 102 residing within three reservoirs 103—a first cavity 102a residing within a first reservoir 103a, a second cavity 102b residing within a second reservoir 103b, and a third cavity 102c residing within a third reservoir 103c. The transfer of the bulk sample of the biofluid across the reservoirs 103a-c is achieved by the biofluid flowing between the respective spaces 105, specifically a first space 105a, second space 105b, and third space 105c formed on the respective peripheral barriers 108. The cartridge 100 further comprises a centre protrusion 115 configured to or cooperating with the connecting spaces 105a-c for the bulk sample of the biofluid to transfer from the loading channel 114 to the reservoirs 103a-c and subsequently the cavities 102a-c.

Figure 2A:
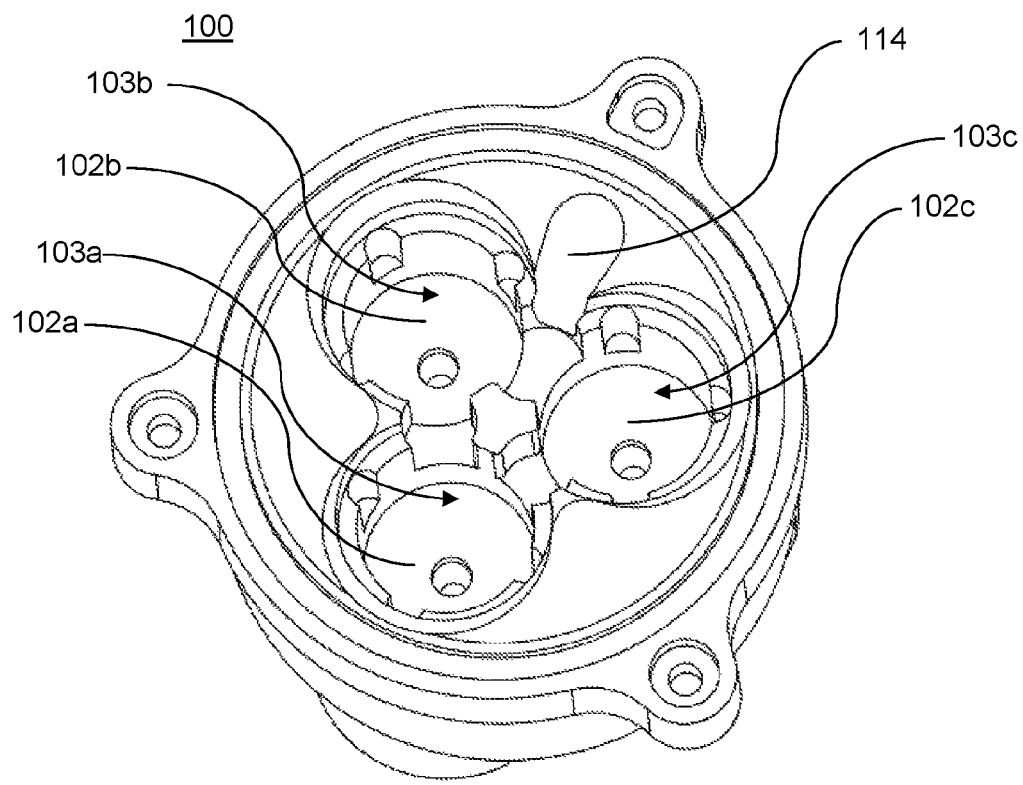
FIG. 2A illustrates a perspective view of a cartridge of an apparatus for dispensing biofluid samples, in accordance with an embodiment of the present disclosure.
Figure 2B:
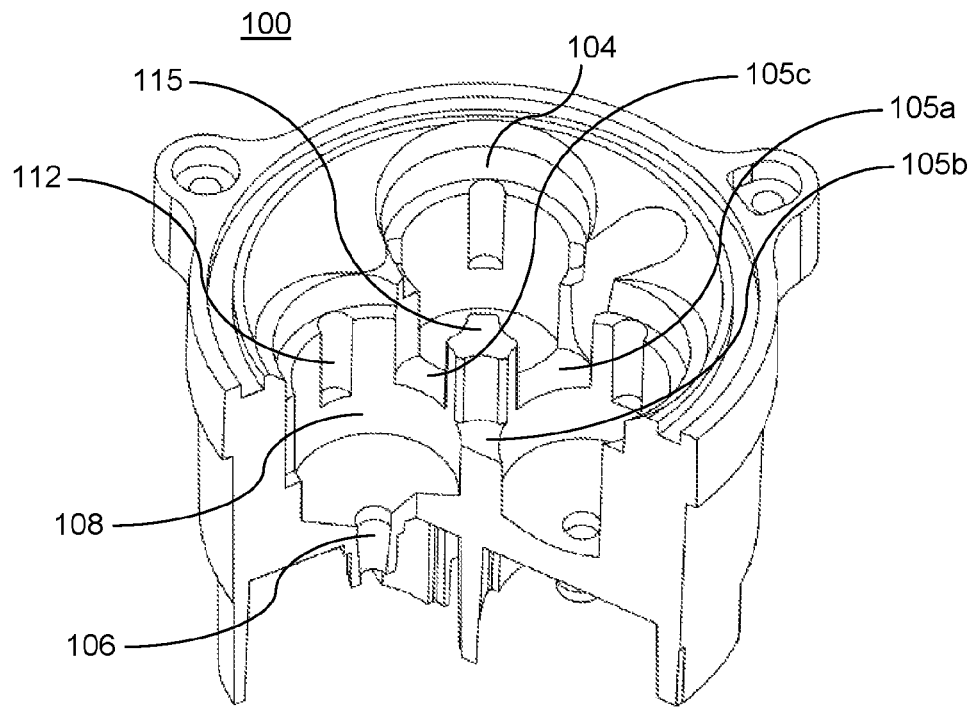
FIG. 2B illustrates a cross-sectional perspective view of the cartridge of FIG. 2A, in accordance with an embodiment of the present disclosure.
Figure 2C:
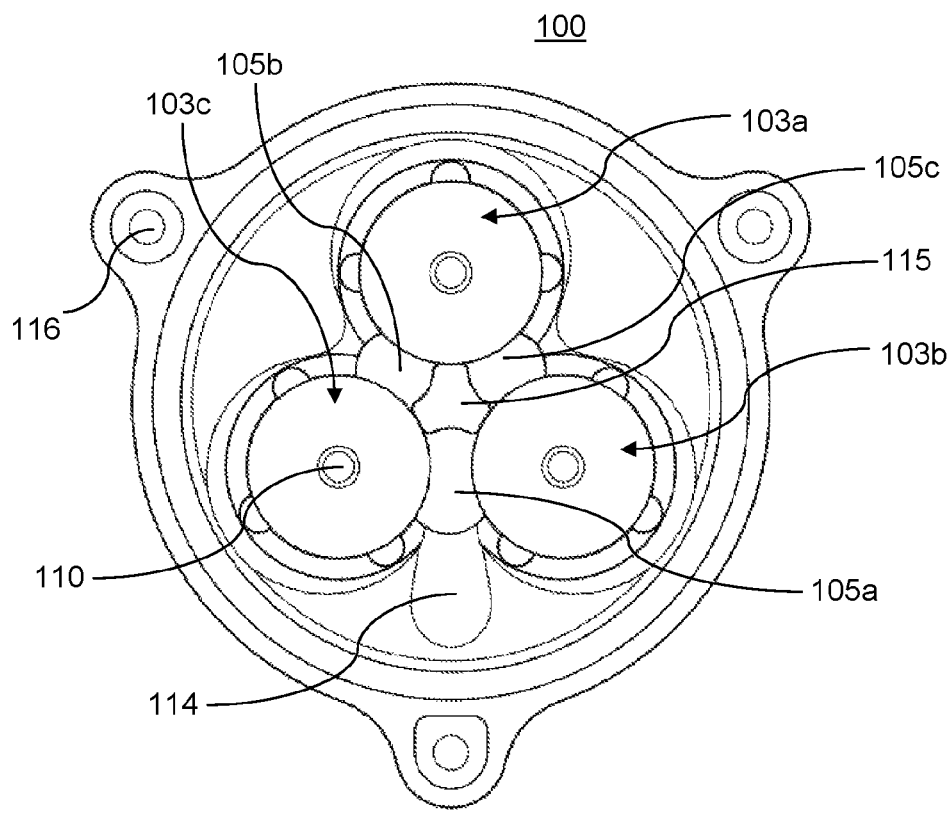
FIG. 2C illustrates a top view of the cartridge of FIG. 2A, in accordance with an embodiment of the present disclosure.
Figure 2D:
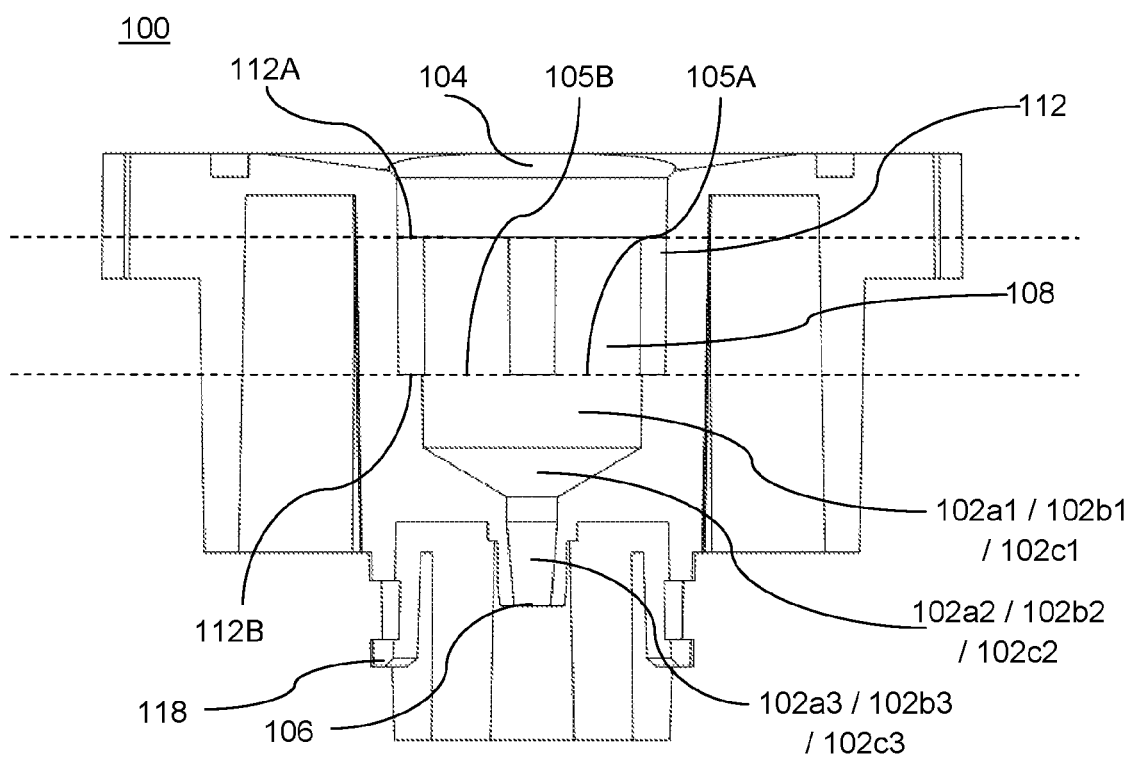
FIG. 2D illustrates a cross-sectional view of the cartridge of FIG. 2A, in accordance with an embodiment of the present disclosure.

The first space 105a connects directly to the loading channel 114 for receiving the biofluid, and may be larger relative to the second space 105b and third space 105c to account for the larger initial flow of the biofluid from the loading channel 114. It would be appreciated that other adjustments may be implemented to account for sudden flow of the biofluid. The skilled person would understand that fluid flows along a least resistive pathway. It may thus be appreciated that, based on the arrangement shown in FIG. 2C, the biofluid would flow substantially simultaneously into the second reservoir 103b and third reservoir 103c first, filling up the second cavity 102b and third cavity 102c, before overflowing towards the first reservoir 103a and consequently filling the first cavity 103a. It may also be appreciated that other variations of the cartridge 100 may enable the bulk sample of the biofluid to flow to the reservoirs 103a-c and cavities 102a-c simultaneously. Referring to FIG. 2D, each cavity 102a/102b/102c is configured to retain a predetermined sample volume of biofluid within a cylindrical space 102a1/102b1/102c1, a conical space 102a2/102b2/102c2, and an outlet space 102a3/102b3/102c3, respectively. It would be appreciated that other shapes and profiles of the spaces 102(a-c)(1-3) are possible.

The biofluid samples contained in the cavities 102 are subsequently dispensable from the cartridge 100 through the valves 110 disposed at the outlets 106 of the cavities 102. Specifically, the biofluid samples are dispensable from the cavities 102 into the cuvettes 200.

Cuvettes 200

The cuvettes 200 are configured for receipt of the biofluid samples dispensable from the cavities 102 of the cartridge 100. Particularly, the cartridge 100 may be configured to receive the biofluid samples and dispense from the cavities 102 into each cuvette 200. Each cuvette 200 may be dispensed with the biofluid sample at substantially the same time as the other cuvettes 200, or alternatively each cuvette 200 may be dispensed with the biofluid sample at staggering times or intervals as the other cuvettes 200.

Referring to FIG. 3A to FIG. 4B, each cuvette 200 is a clear container or tube or combination of container with at least one optically clear window, and with one end sealed or having a mating seal for holding the biofluid sample, such as for performing assays or spectroscopic experiments. Generally, the cuvette 200 may comprise of straight sides or uniform surfaces for more accurate measurement of assay results as there is less optical distortion. However, the profile of the cuvette 200 may differ, such as being of rounded sides or with various cross-sectional shapes. The cuvettes 200 may be made of a plastic, glass, fused quartz material, or a combination of any of the previously mentioned materials.

Each cuvette may be integrated with or coupled/coupleable to at least one cavity 102 at the outlet 106 thereof. For example, a cuvette 200 may be coupled/coupleable to one or more cavities 102, such that the biofluid samples in the one or more cavities 102 are dispensable, preferably simultaneously, into the cuvette 200. In various embodiments, the cuvettes 200 are coupled/coupleable to the cavities 102 such that each cavity 102 is associated or paired with a cuvette 200. The cuvettes 200 may be permanently attached to the cartridge 100, such as by ultraviolet bonding/ultrasonic bonding/adhesive glue. The biofluid sample dispensing apparatus 20 with the cartridge 100 and the permanently attached cuvettes 200 may be used only once and then disposed, i.e. the apparatus 20 is disposable and not reusable.

Alternatively, the cuvettes 200 may be coupleable, i.e. removably or permanently coupled, to the cartridge 100 via a set of latching mechanisms 118 disposed around the outlets 106. As shown in FIG. 3A and FIG. 3B, the cuvettes 200 may comprise latches 206 for latching or attaching to the set of latching mechanisms 118 of the cavities 102. The cuvettes 200 may alternatively comprise an external/internal thread for engagement with an internal/external thread of the cartridge 100, respectively. The same cartridge 100 may be reusable with disposable sets of cuvettes 200, such as with different cuvettes 200 containing different or other reagents. Conversely, the cartridge 100 may be disposable and the same sets of cuvettes 200 may be used with different cartridges 100.

In use, each cuvette 200 contains a reagent, which may be wet (e.g. liquid or aqueous), dry (e.g. solid or powder), or a combination thereof. For example, the reagents in the cuvettes 200 may comprise BCG and DNBA for detecting albumin and creatinine, respectively, and to calculate ACR for diagnosing CKD. One skilled in the art would understand that other reagents may be configured to also diagnose CKD in combination with BCG and DNBA. In various instances of the present disclosure, a cuvette 200 containing DNBA as a reagent is labelled as cuvette 200a, and a cuvette containing BCG as a reagent is labelled as cuvette 200b.

The cuvettes 200 may be pre-deposited or preloaded with the reagents such that the biofluid samples can chemically react with the reagents—forming assay samples—upon their dispensation from the cavities 102. As the biofluid samples are dispensed into the cuvettes 200 together, the reactions can begin at substantially the same time and assay process can also be performed on the assay samples substantially simultaneously. This improves the efficiency of the assay process as multiple assay measurements and results can be obtained at substantially the same time.

In some embodiments, there are three cuvettes 200 corresponding to the number of cavities 102, as shown in the drawings. For calculation of ACR to diagnose CKD, two cuvettes 200b are preloaded with BCG—one for assaying and the other functioning as a comparison control or reference, and the third cuvette 200a is preloaded with DNBA.

Each cuvette 200 further contains one or more magnetic objects 202, e.g. neodymium or ferrite spherical objects or balls, for facilitating physical mixing or agitating of the biofluid sample and reagent in the cuvette 200. Specifically, the magnetic objects 202 are configured to move within the cuvette 200, such as due to application of a magnetic field, thereby physically stirring and mixing the assay sample—comprising the biofluid sample and reagent—within the cuvette 200. Each cuvette 200 is configured to contain at least one magnetic object 202 with a predefined volume of the reagent.

Each cuvette 200 comprises an orifice 204 that is sealed with a hydrophobic membrane. The orifice 204 may be disposed on one of the side surfaces of the cuvette 200 and at a height above the assay sample in the cuvette 200, e.g. near the upper region of the cuvette 200, such that the assay sample is less likely to come into contact with the orifice 204 or the hydrophobic membrane sealing it during mixing or agitation of the assay sample. The hydrophobic membrane is typically thin at around 0.6 μm. The hydrophobic membrane enables gaseous matter, e.g. air, to pass through the orifice 204 but prevents communication of liquids through the orifice 204. Thus, such as by use of a separate vacuum pump, gaseous matter can be extracted from the cuvettes 200 via the orifice and hydrophobic membrane 204. This reduces the formation of bubbles in the assay samples, thereby providing for more accurate measurement of the assay results.

Cover 300

Figure 4A:
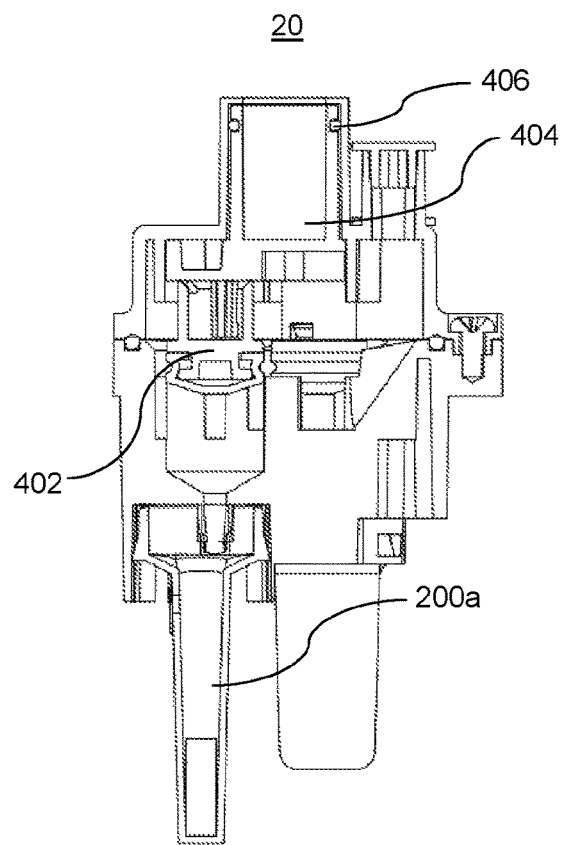
FIG. 4A illustrates a cross-sectional view of an apparatus for dispensing biofluid samples, particularly in relation to a DNBA-loaded cuvette, in accordance with an embodiment of the present disclosure.
Figure 4B:
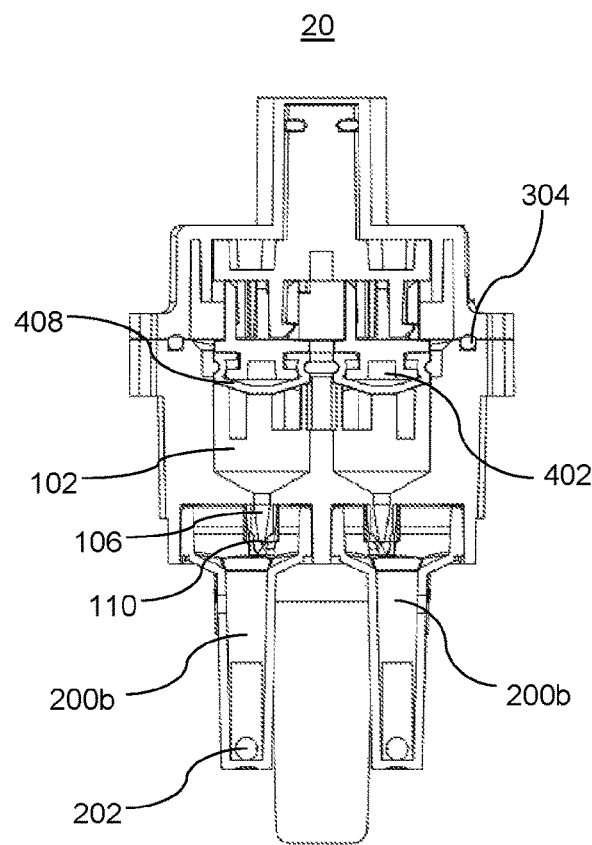
FIG. 4B illustrates another cross-sectional view of the apparatus of FIG. 4A, particularly in relation to BCG-loaded cuvettes, in accordance with an embodiment of the present disclosure.

The cover 300 is configured for covering the cartridge 100, particularly during dispensation of the biofluid samples into the cuvettes 200. Referring to FIG. 2C, the cartridge 100 comprises fasteners 116 arranged around the cartridge 100 for coupling, joining, or connecting to the cover 300. The fasteners 116 may comprise at least one protrusion positioned circumferentially for alignment of the cover 300 and the cartridge 100. The fasteners 116 may comprise bolt or screw holes, or latching mechanisms as readily understood by the skilled person. Alternatively, male and female latches may be positioned on the cartridge 100 and the cover 300 for mating engagement. Referring to FIG. 3A and FIG. 3B, the cover 300 comprises similar or matching fasteners 302 that correspond to the fasteners 116 of the cartridge 100 for coupling the cover 300 to the cartridge 100. Referring to FIG. 4A and FIG. 4B, in order to provide sealing engagement between the cartridge 100 and the cover 300, the apparatus 20 further comprises a cover sealing element 304 disposed on the cartridge 100 or the cover 300, such as an O-ring or gasket made with a silicon or rubber material. The cover sealing element 304 seeks to prevent leakage of biofluid from inside the cartridge 100 (covered by the cover 300) when the biofluid overflow the inlets 104 into a space confined within the cartridge 100.

The cover 300 comprises a loading port 306 for receiving a bulk sample of biofluid. Particularly, when the cartridge 100 is covered by the cover 300, the user may load the bulk sample of biofluid into the cavities 102 of the cartridge 100 via the loading port 306 of the cover 300. The loading port 306 is aligned with the loading channel 114 of the cartridge 100, such that the bulk sample of biofluid is distributed into the cavities 102 upon entry via the loading port 306. The loading port 306 configured to a funnel or conical shape to further enhance gravitational effect, thus, further guiding the bulk sample of biofluid to the cavities 102. The loading channel 114 guides the bulk sample of biofluid to the cavities 102. The cover 300 further comprises a cap 308 for closing or sealing the loading port 306, preventing entry of fluids into or leakage of fluids out of the cartridge 100.

The cover 300 further comprises one or more air vents 310, and each air vent 310 is sealed with a hydrophobic membrane with a thickness of around 0.5 to 1 μm or more particularly 0.6 μm for example. The hydrophobic membranes enable gaseous matter to pass through the air vents 310 but prevent communication of liquids through the air vents 310. The air vents 310 and the hydrophobic membranes enable air inside the cartridge 100 to be displaced out as the user loads the cartridge 100 with the bulk sample of biofluid via the loading port 306. By displacing the air out, the air vents 310 prevent pressure from building up inside the cartridge 100.

The cover 300 further comprises a channel 312 at a central portion thereof for receiving an actuator, such as that of a separate dispensing system. The channel 312 is coaxial with the central vertical axis of the cartridge 100. The channel 312 may be of a tubular profile or of other cross-sectional shapes. The actuator is configured for actuating the piston assembly 400 to dispense the biofluid samples from the cavities 102 into the cuvettes 200.

Piston Assembly 400

Referring to FIG. 4A and FIG. 4B, the piston assembly 400 comprises a set of pistons/shafts/plungers 402 connected to a central piston 404. The central piston 404 resides within the channel 312 of the cover 300 and is coaxial with the central vertical axis of the cartridge 100. During operation, the actuator comes into contact with and displaces the central piston 404, consequently displacing the pistons 402 into the reservoirs 103 and cavities 102 for dispensing the biofluid samples from the cavities 102. Further, during operation, the air vents 310 enable air outside the cover 300 to be displaced inside through the hydrophobic membranes as the pistons 402 are being displaced. By displacing the air inside, the air vents 310 allow positive pressure displacement within the cartridge 100, thus, allowing the plunging or forward movement effect of the pistons 402.

In an alternative embodiment, the central piston 404 may be configured to include a set of equally-cut sections, which when combined together, represents the central piston 404. Each of the equally cut sections may be having a different step or depth or height configured to deliver a step wise plunging effect for time-separate communication for dispensing the biofluid samples, i.e. the biofluid samples in the cavities 102 are displaced at different times from one another but by the same actuating effect from the central piston 404. Yet alternatively, the dimensions of the pistons 402 may be varied to achieve a similar effect.

Similar to the cuvettes 200, each piston 402 is associated or paired with a cavity 102. In some embodiments, there are three pistons 402 corresponding to the number of cavities 102, as shown in the drawings. Each piston 402 is displaceable within the respective reservoir 103 and cavity 102, particularly between the inlet 104 and outlet 106 thereof, for exerting pressure on the biofluid sample contained in the cavity 102 and dispensing the biofluid sample through the valve 110. The displacement of the pistons 402 in the cavities 102 is similar to the displacement of a plunger in a syringe.

Each valve 110 may be positioned directly at the centre of the respective cavity 102. Alternatively, each valve 110 may be positioned offset from the centre of the respective cavity 102, e.g. closer to the central vertical axis of the cartridge 100. This may enable the cuvettes 200 to be positioned more closely together, reducing the overall spatial footprint of the apparatus 20. Further, the valves 110 are also positioned closer to the central piston 404, which may improve the effectiveness of dispensing the biofluid samples under force of the central piston 404.

The piston assembly 400 further comprises a piston sealing element 406 disposed around the central piston 404 to provide sealing engagement at the interface of the central piston 404 with the channel 312. The piston sealing element 406 may be or comprises an O-ring or gasket made with a silicon or rubber material. The piston sealing element 406 seeks to prevent leakage of biofluid from inside the cartridge 100 when central piston 404 is being displaced to move the pistons 402 for dispensing the biofluid samples.

Each piston 402 comprises or is capped with a piston end 408 at the bottom of the piston 402. The piston ends 408 may be or comprise an O-ring or gasket made of a soft resilient material, e.g. rubber or silicon. The piston ends 408 function as stoppers when the pistons 402 are displaced to the lower part of the cavities 102, i.e. the outlets 106. It would be appreciated by the skilled person that the piston ends 408 operate similarly to the plungers in syringes. Particularly, the piston ends 408 provide sealing engagements at the interfaces of the pistons 402 with the reservoirs 103, or more specifically with the peripheral barriers 108, during displacement of the pistons 402 within the reservoirs 103. The piston ends 408 seek to prevent leakage of biofluid samples from inside the cavities 102 and reservoirs 103 when the pistons 402 are exerting pressure on the biofluid samples, thereby ensuring that the biofluid samples are discharged from the cavities 102 only through the valves 110. Additionally, the piston ends 408 may soften the impact caused by the pistons 402 on the outlets 106 of the cavities 102, significantly preventing or at least mitigating risk of damage to the pistons 402 and the cavities 102.

Use of Biofluid Sample Dispensing Apparatus 20

In various embodiments, the biofluid sample dispensing apparatus 20 is used for dispensing biofluid samples to be assayed. For the cartridge 100 of the biofluid sample dispensing apparatus 20 to be loaded with or receive a bulk sample of biofluid, a user may first collect a biofluid, e.g. urine, in any type of cup or container. For example, at least 10 ml of the biofluid may be collected in a cup. A commercial disposal syringe or pipette may then be used to load the biofluid from the cup. For example, the syringe or pipette may hold at least 5 ml of the biofluid. The same syringe or pipette is then used to dispense a bulk sample of the biofluid into the loading port 306 at the cover 300.

The apparatus 20 may comprise machine-readable code, such as a conventional barcode, matrix barcode, or radio frequency identification (RFID) tag, for providing information on the biofluid. This information may include, but is not limited to, information, content, and/or composition of the reagent(s). This information may additionally include details about the apparatus 20, such as the specifications and operation instructions of various components of the apparatus 20.

After loading, the bulk sample of biofluid is communicated via the loading port 306 to the loading channel 114 and distributed to the reservoirs 103 and cavities 102. The reservoirs 103 are linked together and fluidly communicable with one another above their peripheral barriers 108, e.g. at their inlets 104. Thus, the amount of the bulk sample of biofluid loaded into the cartridge 100 has to sufficiently cover over the peripheral barriers 108 in order for the biofluid to flow around and fill up the cavities 102. For example, if there are three cavities 102a-c as shown in the drawings and each cavity 102a/102b/102c is configured to hold/contain a predetermined or metered volume of 1 ml of biofluid sample, then dispensing 5 ml of biofluid from the syringe/pipette as the bulk sample of biofluid would sufficiently cover over the peripheral barrier 108 of the respective reservoir 103, and ensure each cavity 102 would be totally filled with biofluid sample.

The overflow outlet 112 of each reservoir 103 allows gaseous matter or air to be displaced out from the reservoir 103 when the biofluid is filling the reservoir 103 and cavity 102. This minimizes or at least reduces the air trapped inside the reservoir 103/cavity 102, which may cause the cavity 102 to contain an inaccurate amount or volume of a biofluid sample. As each cavity 102 is being filled with the biofluid, the overflow outlet 112 also predetermines/limits/meters the precise volume or amount of the biofluid sample to be contained in the cavity 102. The overflow outlet 112 allows excess volumes of the biofluid (above the predetermined/metered volume, e.g. 1 ml) to be channelled away from the reservoir 103 during plunging effect by a piston 402.

In some situations such as due to high viscosity of the biofluid, excess volumes of the biofluid may be not readily discharged from the overflow outlets 112. During operation of the piston assembly 400, a piston 402 may exert pressure on the biofluid in a reservoir 103 and force the excess volumes (e.g. beyond 1 ml) to be discharged from the overflow outlet 112. Discharge of the excess volumes will stop when the piston 402 reach the overflow outlet 112, specifically when the piston end 408 reaching the lower plane 112B of the overflow outlet 112. At this lower plane 112B, the amount of biofluid sample contained within the cavity 102 between the piston end 408 and the valve 110 is the predetermined volume, e.g. 1 ml.

It would be appreciated that a cavity 102 may contain a different amount of biofluid sample, such as but not limited to 0.4-2 ml. A cavity 102 may also not contain the same amount of biofluid sample as one or more other cavities 102. The total volume of biofluid loadable into the cartridge 100 may also vary, such as depending on the number and/or arrangement of the cavities 102, the predetermined volume of biofluid sample required in each cavity 102, volume of each reservoir 103 and space 105, and/or volume of the space between the cover 300 and the cartridge 100.

Figure 5A:
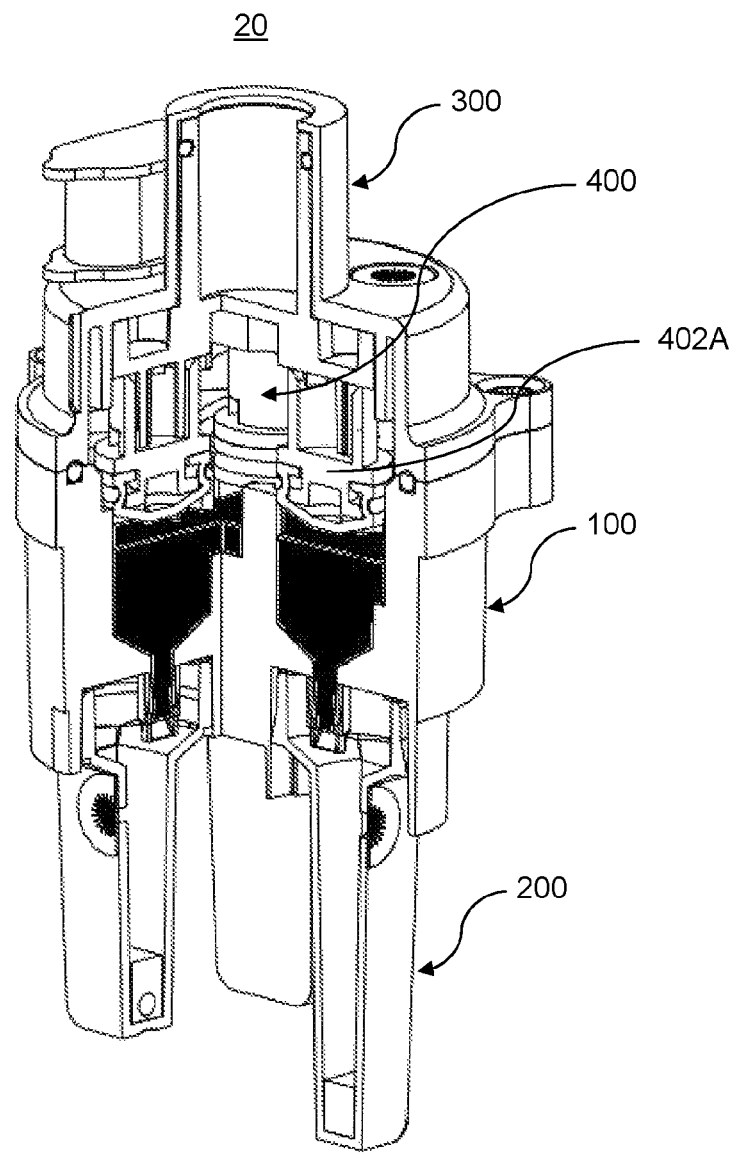
FIG. 5A illustrates a cross-sectional perspective view of an apparatus for dispensing biofluid samples, particularly in relation to pistons in an undisplaced state, in accordance with an embodiment of the present disclosure.
Figure 5B:
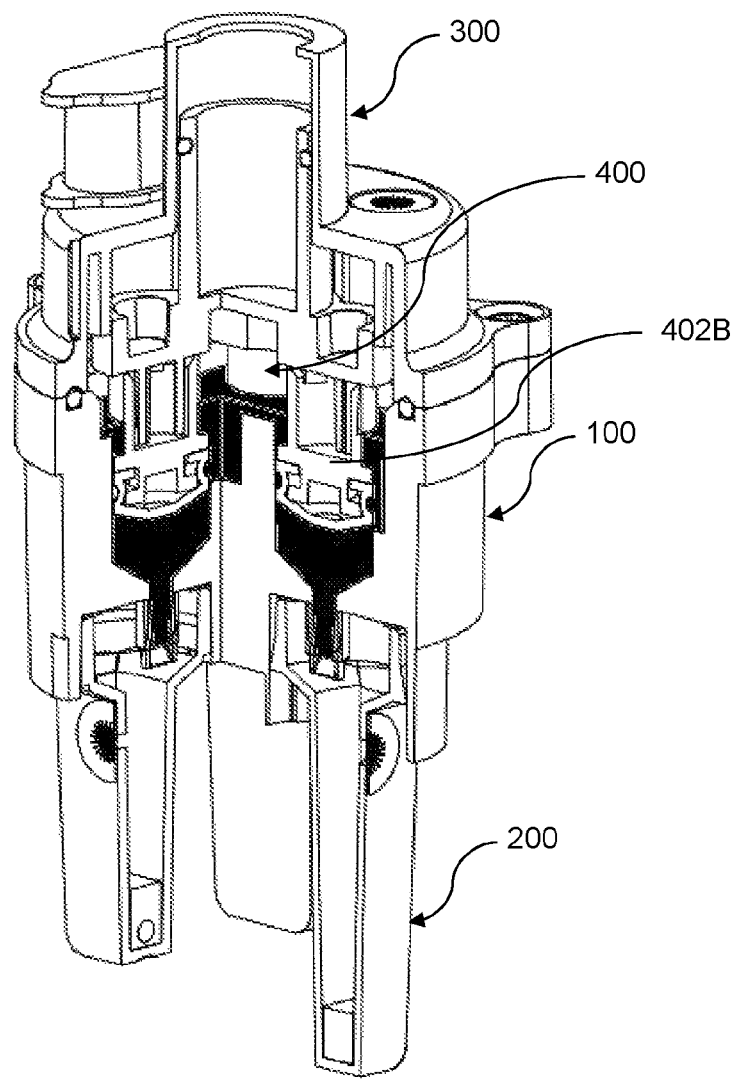
FIG. 5B illustrates another cross-sectional perspective view of the apparatus of FIG. 5A, particularly in relation to pistons in a partially displaced state, in accordance with an embodiment of the present disclosure.

Referring to FIG. 5A, the cavities 102 are filled with biofluid loaded by the user and the pistons 402 are in an undisplaced or unactuated state (402A). The biofluid is indicated by the black shading. The biofluid samples in the cavities 102 are more than the predetermined volumes. During actuation, excess volumes of the biofluid may be allowed to naturally discharge from the overflow outlets 112. Alternatively with reference to FIG. 5B, the piston assembly 400 may be operated with an actuator from a separate dispenser apparatus. The central piston 404 and the pistons 402 would be displaced downwards, i.e. to a partially displaced/actuated state (402B), and the excess volumes would be forced out of the overflow outlets 112. As shown in FIG. 5B, when the piston ends 408 reach the lower planes 112B of the overflow outlets 112, the remaining volumes of biofluid in each cavity 102 is the predetermined/metered volume of biofluid sample for subsequent dispensation.

Figure 5C:
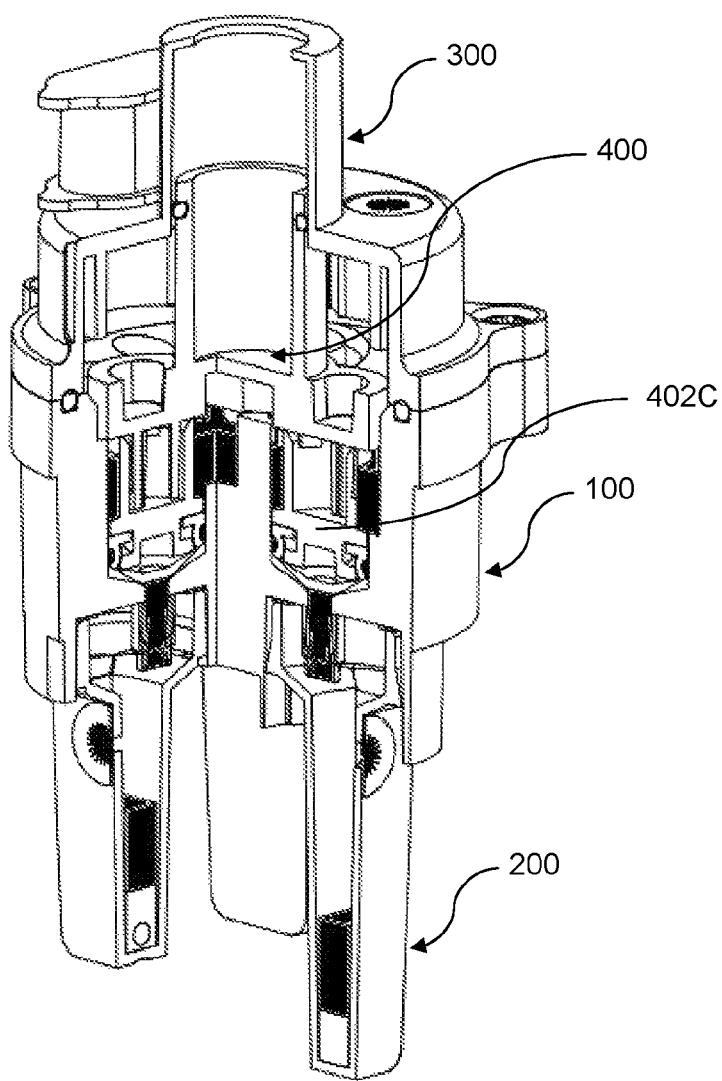
FIG. 5C illustrates another cross-sectional perspective view of the apparatus of FIG. 5A, particularly in relation to pistons in a fully displaced state, in accordance with an embodiment of the present disclosure.
Figure 5D:
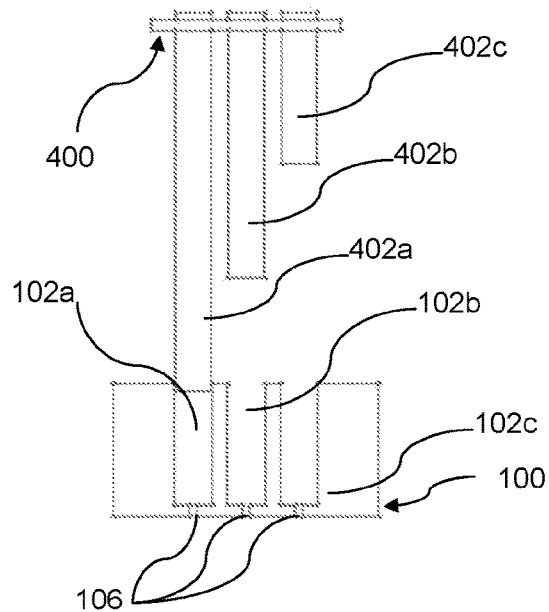
FIG. 5D to FIG. 5G illustrate cross-sectional views of an alternative piston assembly with staggered pistons of different lengths, in accordance with an embodiment of the present disclosure.
Figure 5E:
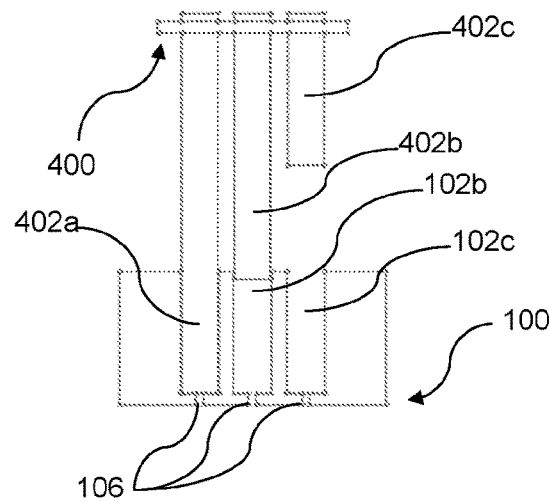
Figure 5F:
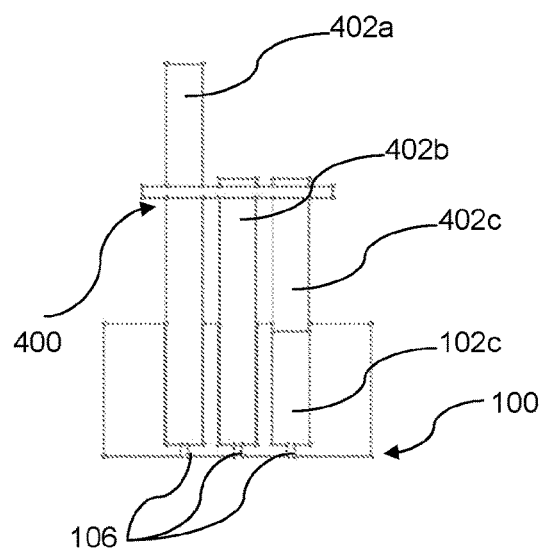
Figure 5G:
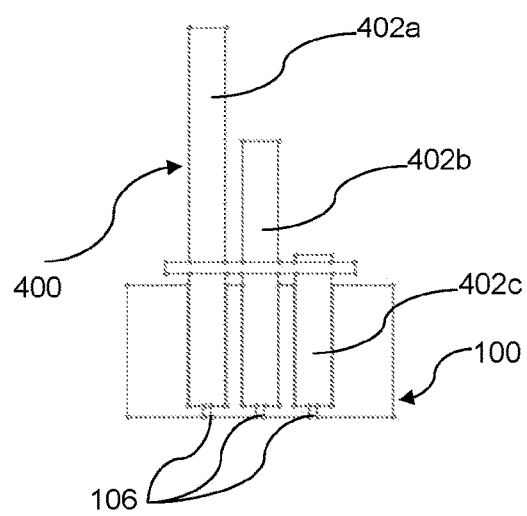

Referring to FIG. 5C, as the pistons 402 are being further displaced downwards by the actuator, i.e. to a fully displaced/actuated state (402C), to dispense the biofluid samples from the cavities 102, the biofluid samples become pressurized by the positive pressure from the pistons 402. The positive pressure is transferred to the valves 110 and if the positive pressure is above the threshold pressure of the valves 110, the valves 110 would change from the default closed state to the open state. In the open state, the valves 110 enable the biofluid samples to be dispensed from the cavities 102 to the cuvettes 200. As the pistons 402 continue to move downwards to push out the biofluid samples, air would be displaced out from the cartridge 100 via the air vents 310, thereby preventing pressure build-up in the cartridge 100. This would also minimize or mitigate risk of the biofluid samples overflowing or spilling out of the cartridge 100 during dispensation. As shown in FIG. 5C, the cuvettes 200 contain the biofluid samples (indicated by black shading) dispensed from the cavities 102.

It would be appreciated that the actuator may exert a higher positive pressure on the pistons 402 and increase the flow rate of the biofluid samples through the valves 110. Alternatively, the valves 110 may be made more resilient, such as with a stronger material or biasing mechanism to better maintain the valves 110 in the closed state, and decrease the flow rate of the biofluid samples through the valves 110. Accordingly, the actuator and/or valves 110 are individually configurable or co-operable together to control the time or duration of dispensation of the biofluid samples. For example, in some situations such as depending on the reagents in the cuvettes 200, the biofluid samples may be slowly and continually dispensed into the cuvettes 200, e.g. to increase the chemical reaction time with the reagents. In other situations, the biofluid samples may be quickly and completely dispensed into the cuvettes 200.

A piston 402 may also be of a different length than others, e.g. longer, so that the biofluid sample in the cavity 102 associated with this piston 402 can be dispensed first before the other biofluid samples, given that all the pistons 402 are displaced at substantially the same time. FIG. 5D to FIG. 5G illustrates the sequence of actuation of a piston assembly 400 having pistons 402a-c of different lengths. The pistons 402a-c are actuated at the same time into the cavities 102. Due to the different lengths, some cavities 102 will have their biofluid sample dispensed first. The dispensation of the biofluid samples from the cavities 102 can be staggered or dispensed at intervals in this manner. The biofluid samples are thus dispensed from the cavities 102a-c by the respective pistons 402a-c in a stepwise manner. The sequence of dispensation of the biofluid samples from the cavities 102a-c may be configurable to achieve different sequences of "steps" by modifying the pistons 402a-c accordingly. Thus, precise time or duration control for biofluid sample to reagent interaction may be achieved with the actuator and/or piston assembly 400.

Therefore, the biofluid sample dispensing apparatus 20 has a multi-piston assembly 400 and a multi-cavity cartridge 100, providing for dividing and apportioning different volumes of biofluid samples in the cavities 102 before releasing or dispensing the biofluid samples into the cuvettes 200 with different pre-deposited reagents, e.g. BCG and DNBA. Each cavity 102 resides within a reservoir 103 having an overflow outlet 112 to limit/control/meter the predetermined volume of biofluid sample to be dispensed through the valve 110. The piston assembly 400 with multiple pistons 402, combined with the multi-cavity cartridge 100 with individual valves 110 attached to the output portions 106, is used to control the time/duration of dispensation. The design of the biofluid sample dispensing apparatus 20 seeks to provide a low cost, simple, and compact solution for metering and dispensing biofluid samples that can be integrated with the cuvettes 200 preloaded with reagents. In addition, the biofluid sample dispensing apparatus 20 may comprise disposable consumables, such as the cartridge 100 and cuvettes 200. This may potentially reduce the cost of and improve the manufacturing process.

The biofluid samples dispensed by the biofluid sample dispensing apparatus 20 may subsequently be assayed with a biofluid assay apparatus 30. The biofluid assay apparatus 30 may comprise an automated system for performing an assay process on assay samples comprising the biofluid samples and reagents, minimizing or at least reducing manual user intervention. An automated environment could advantageously improve the efficiency of the assay process performed on the assay samples.

Biofluid Assay Apparatus 30

Figure 6A:
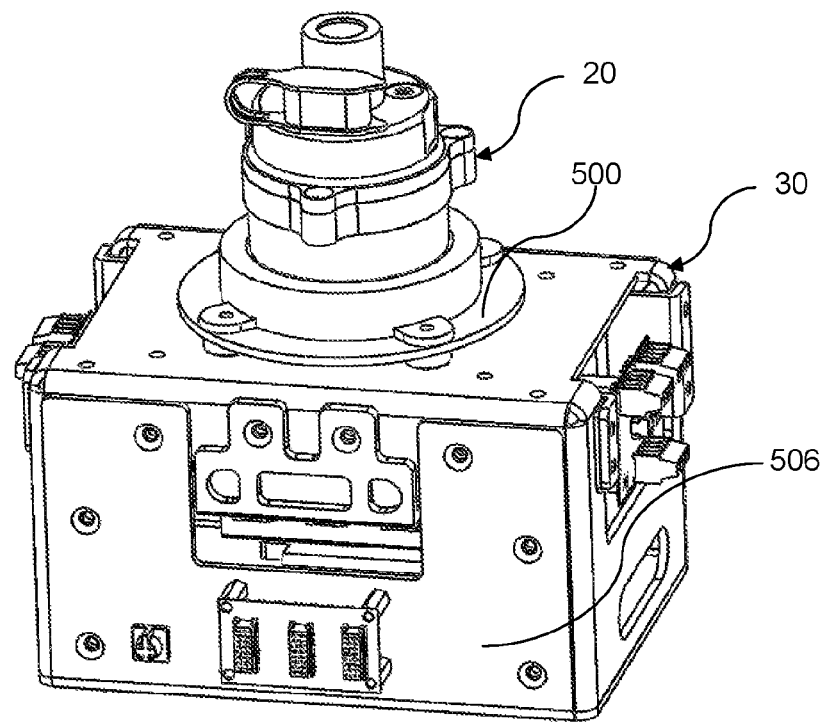
FIG. 6A illustrates an external view of an apparatus for assaying biofluid, in accordance with an embodiment of the present disclosure.
Figure 6B:
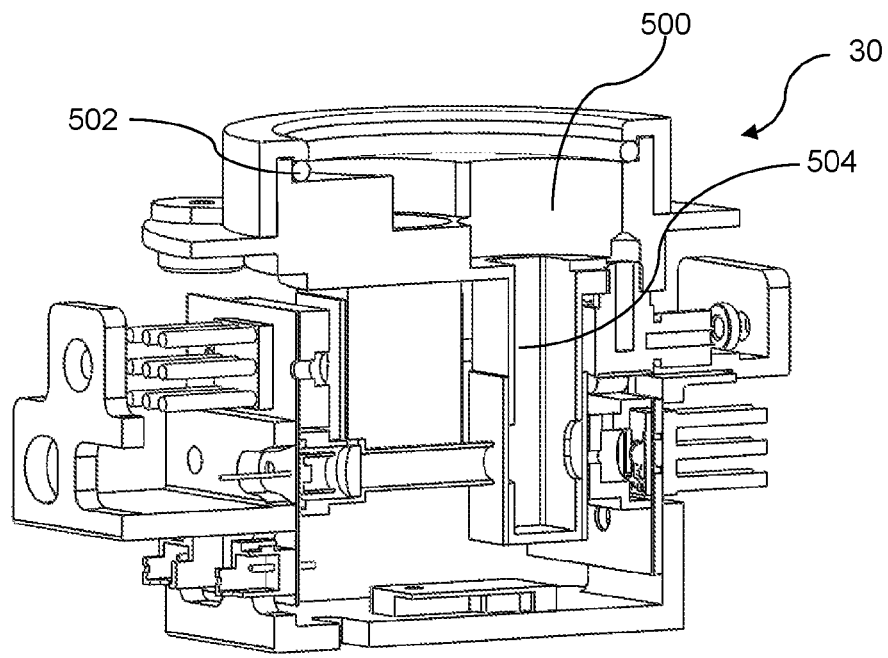
FIG. 6B illustrates an internal view of the apparatus of FIG. 6A, in accordance with an embodiment of the present disclosure.
Figure 6C:
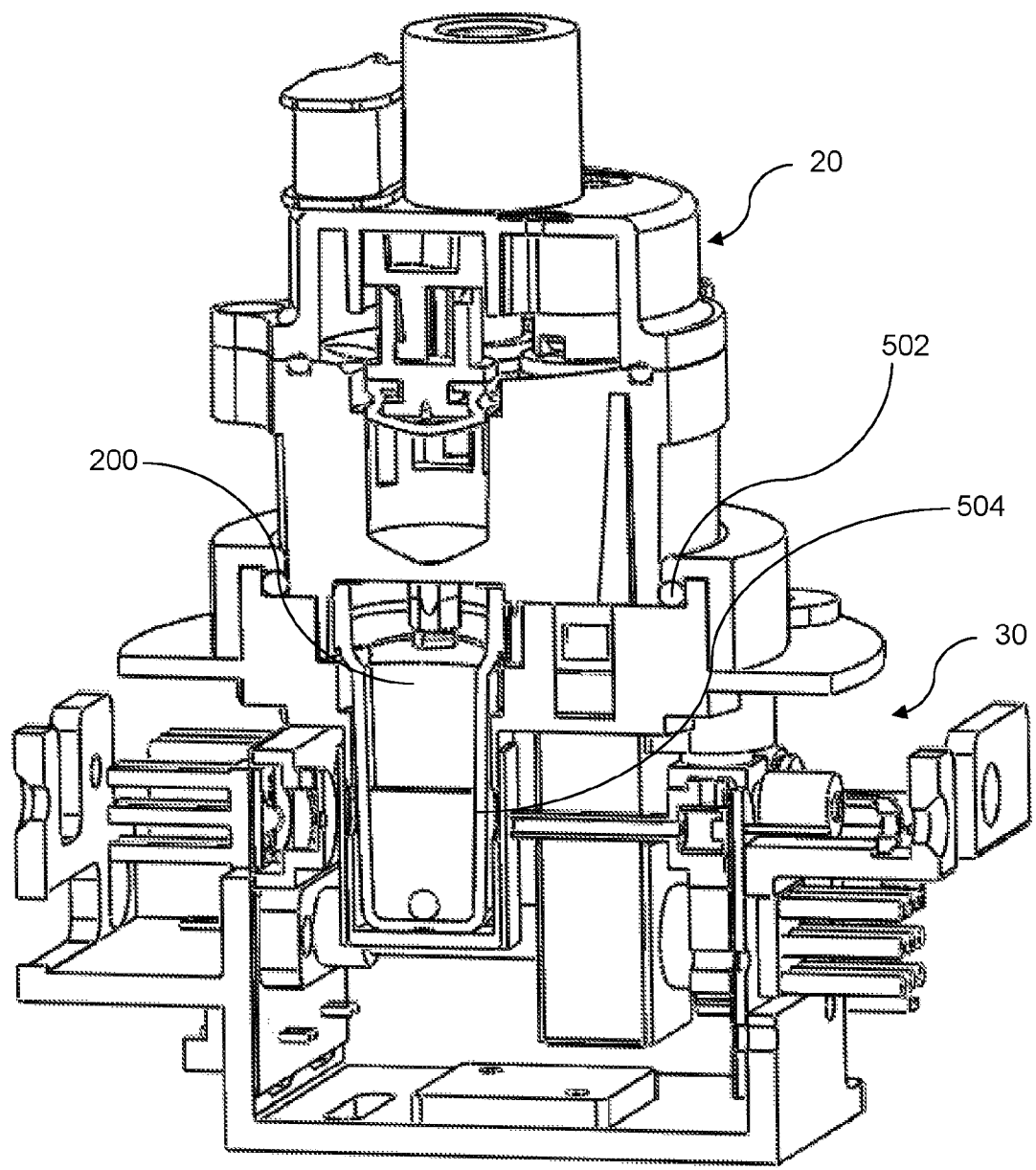
FIG. 6C illustrates an internal view of the apparatus of FIG. 6A assembled with an apparatus for dispensing biofluid samples, in accordance with an embodiment of the present disclosure.

In representative or exemplary embodiments of the present disclosure, there is an apparatus 30 for assaying biofluid or a biofluid assay apparatus 30 as illustrated in FIG. 6A to FIG. 6C. The biofluid assay apparatus 30 comprises a receptacle 500 for housing a set of cuvettes 200 of a biofluid sample dispensing apparatus 20, each cuvette 200 being configured for containing an assay sample comprising a reagent and a sample of the biofluid. Particularly, the cuvettes 200 may be housed in the receptacle 500 or a chamber/space inside the receptacle 500. The biofluid assay apparatus 30 further comprises an automated system connected to the receptacle 500 for performing an assay process on the assay samples in the cuvettes 200, while maintaining the cuvettes 200 within the receptacle 500. The biofluid assay apparatus 30 further comprises a receptacle sealing element 502 for providing sealing engagement between the receptacle 500 and the biofluid sample dispensing apparatus 20 for sealing the cuvettes 200 within the receptacle 500. The receptacle sealing element 502 may be disposed around the receptacle 500, and may be or comprises an O-ring or gasket made with a silicon or rubber material. The receptacle sealing element 502 seeks to provide a vacuum seal from inside the receptacle 500. Where appropriate, various components of the apparatus 30 are assembled together with sealing elements to provide the vacuum seal or at least mitigate leakage of biofluid. Such sealing elements may include, but are not limited to, O-rings or gaskets made of resilient materials, rubber/silicon tight fitting connections, ultraviolet bonding/ultrasonic bonding/adhesive glue, latching, cantilever, etc.

The receptacle 500 further comprises a set of receptacle sockets 504 for mating engagement with the cuvettes 200. Similar to the cavities 102 and pistons 402, each cuvette 200 may be associated or paired with a receptacle socket 504. In some embodiments, there are three receptacle sockets 504 for receiving the cuvettes 200, as shown in the drawings. Further, for each pair of receptacle socket 504 and cuvette 200, their profiles or shapes may be substantially congruent to each other such that the cuvettes 200 are insertable into/receivable by the receptacle sockets 504 in only one orientation. More broadly, the receptacle sockets 504 may be arranged such that the biofluid sample dispensing apparatus 20 is insertable into/receivable by the receptacle 500 in only one orientation. Specifically, the biofluid sample dispensing apparatus 20 can be inserted into/received by the receptacle 500 of the biofluid assay apparatus 30 in one orientation and direction only. Insertion in any other orientation or direction would not allow complete insertion of the cuvettes 200 and the biofluid sample dispensing apparatus 20 would not be stably supported in the receptacle 500.

In addition to or instead of the receptacle sealing element 502 around the receptacle 500, each receptacle socket 504 may comprise a similar receptacle socket sealing element for providing a vacuum seal from inside the receptacle 500. Each receptacle socket sealing element provides sealing engagement at the interface of the cuvette 200 with the receptacle socket 504.

Further, the receptacle sockets 504 may be arranged such that the assay process is performable on the assay samples in the cuvettes 200 substantially simultaneously. Particularly, when the cuvettes 200 are sealed within the receptacle 500, the assay process can be performed on all of the assay samples in the cuvettes 200 at substantially the same time, thereby improving the performance efficiency of the assay process.

The assay process is performed/performable by the automated system which comprise at least one of an electromagnetic control system 650, an optical system 700, and a temperature control system 750. Various components of the automated system may be housed within the biofluid assay apparatus 30 which may further comprise a body casing 506 made of sheet metal. The body casing 506 provides structural support to the biofluid assay apparatus 30 and also protects components of the automated system. It would be appreciated that the body casing 506 may be made of other materials with similar structural integrity as sheet metal.

Figures 7A, 7B:
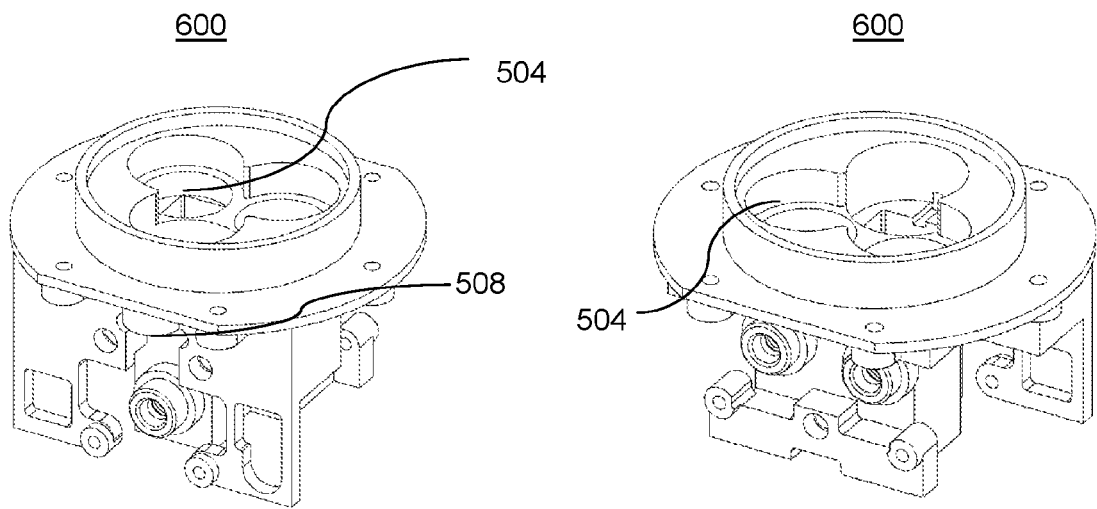
FIG. 7A illustrates a perspective view of a receptacle of an apparatus for assaying biofluid, in accordance with an embodiment of the present disclosure.
FIG. 7B illustrates another perspective view of the receptacle of FIG. 7A, in accordance with an embodiment of the present disclosure.
Figure 7C:
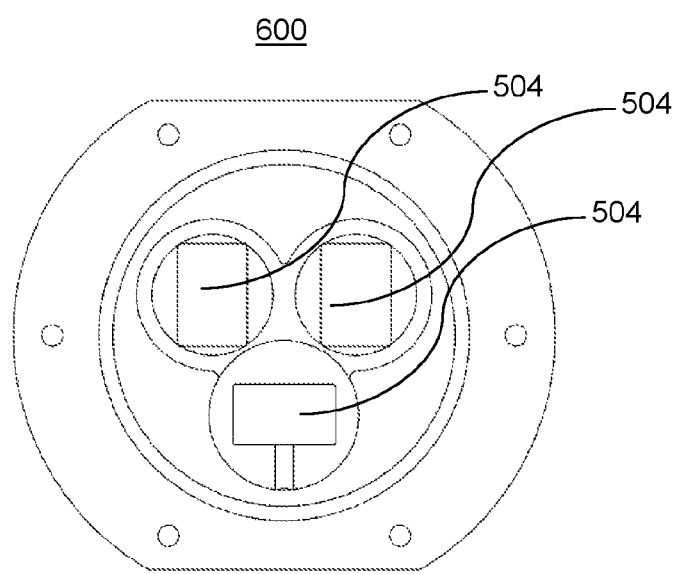
FIG. 7C illustrates a top view of the receptacle of FIG. 7A and FIG. 7B, in accordance with an embodiment of the present disclosure.

Referring to FIG. 7A to FIG. 7C, the receptacle 500 may be configured to undergo an evacuation process in or as part of the assay process. The evacuation of the receptacle 500 creates a sealed environment for the cuvettes 200 and consequently evacuates gaseous matter from within the cuvettes 200. The receptacle sealing element 502 provides for improved sealing engagement between the biofluid sample dispensing apparatus 20 and the receptacle 500 to improve efficiency of the evacuation process. Accordingly, when the biofluid sample dispensing apparatus 20 is inserted into the biofluid assay apparatus 30, i.e. when the cuvettes matingly engage with the receptacle sockets 504, the cuvettes 200 would be housed in the receptacle 500 which is substantially sealed to prevent or mitigate leakage of fluids, including air.

In some embodiments, each receptacle socket 504 functions as a vacuum chamber and provides a substantially sealed environment for the respective cuvette 200. The receptacle 500 comprises a vacuum port 508 for evacuation to thereby create a vacuum environment for the respective cuvette 200.

The apparatus 30 may further comprise a separate vacuum pump or vacuum source for substantially evacuating the receptacle sockets 504. More specifically, the vacuum pump is operable for substantially evacuating the cuvettes 200 residing in the receptacle sockets 504 via the vacuum ports 508. Each vacuum port 508 is connected to the vacuum pump by a conduit, e.g. a tubing or hose, for the evacuation process.

In some alternative embodiments, the receptacle sockets 504 may be configured such that they are integrated as a single vacuum chamber while still allowing the cuvettes 200 to be inserted in only one orientation. The receptacle sockets 504 may thus share a common conduit connectable to the vacuum pump for the evacuation process. The vacuum pump may be of a brushless diaphragm type with a maximum degree rating of around 25 to 28 Hg.

During the evacuation process, the vacuum pump creates negative vacuum pressure relative to the receptacle sockets 504 and gaseous matter, particularly air and water vapour, is extracted from the receptacle sockets 504. Further, any presence of water vapour in the conduits would also be removed by the negative vacuum pressure, thereby avoiding contamination of the assay samples by the water vapour.

As the cuvettes 200 are residing in the receptacle sockets 504, any gaseous matter contained in the cuvettes 200 would be extracted. Specifically, the gaseous matter is extracted through the orifices 204 of the cuvettes 200, each of which is sealed with a hydrophobic membrane with a thickness of around 0.5 to 1 μm or more particularly 0.6 μm for example. The hydrophobic membranes allow the negative vacuum pressure to pass through into the cuvettes 200, and consequently allow gaseous matter to be extracted from the cuvettes 200. The evacuation of only gaseous matter from the cuvettes 200 via the hydrophobic membranes prevents the liquid assay samples from leaking out of the cuvettes 200. This reduces the formation of bubbles in the assay samples. Particularly, there is minimal to no bubbles formed during physical mixing of the assay samples.

It would be appreciated that the evacuation process may be controlled by a central or main printed circuit board (PCB) or mainboard of the apparatus 30. The main PCB may further comprise or be attached to a layer of silicone thermal for dissipation of heat.

Electromagnetic Control System 650

After dispensing the biofluid samples into the cuvettes 200 which are preloaded with the reagents, the assay samples comprising the biofluid samples and reagents may need to be mixed well together to homogenize the assay samples.

Figure 8A:
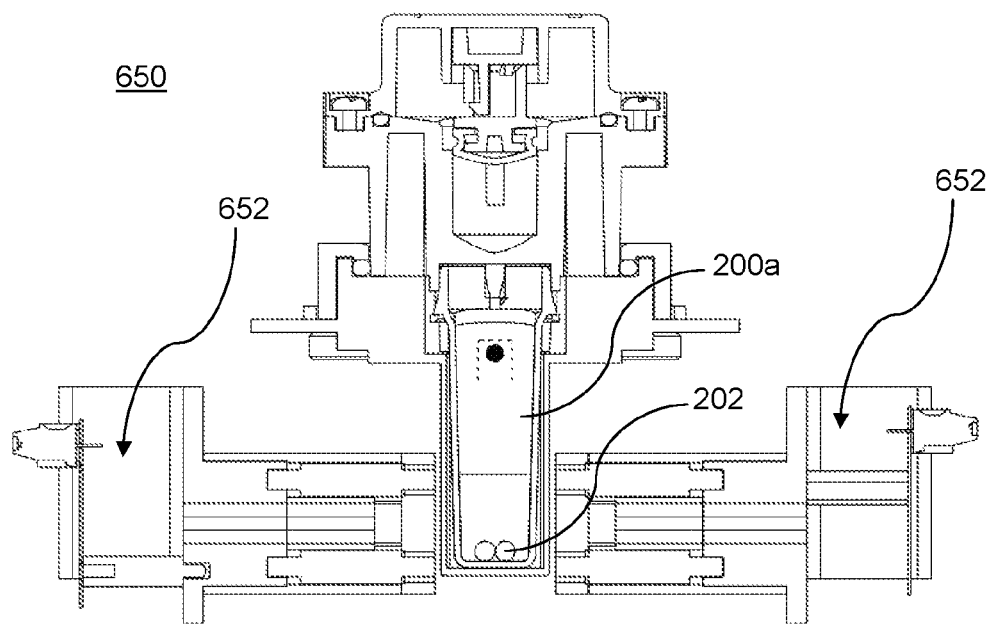
FIG. 8A illustrates a cross-sectional view of an electromagnetic control system of an apparatus for assaying biofluid, particularly in relation to a DNBA-loaded cuvette, in accordance with an embodiment of the present disclosure.
Figure 8B:
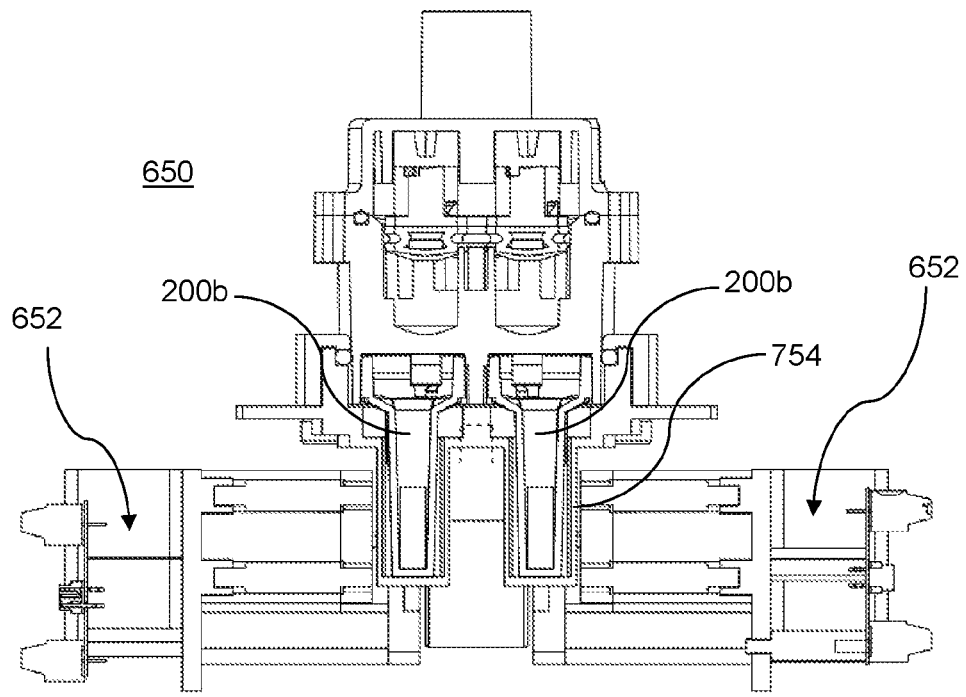
FIG. 8B illustrates another cross-sectional view of the electromagnetic control system of FIG. 8A, particularly in relation to BCG-loaded cuvettes, in accordance with an embodiment of the present disclosure.
Figure 8C:
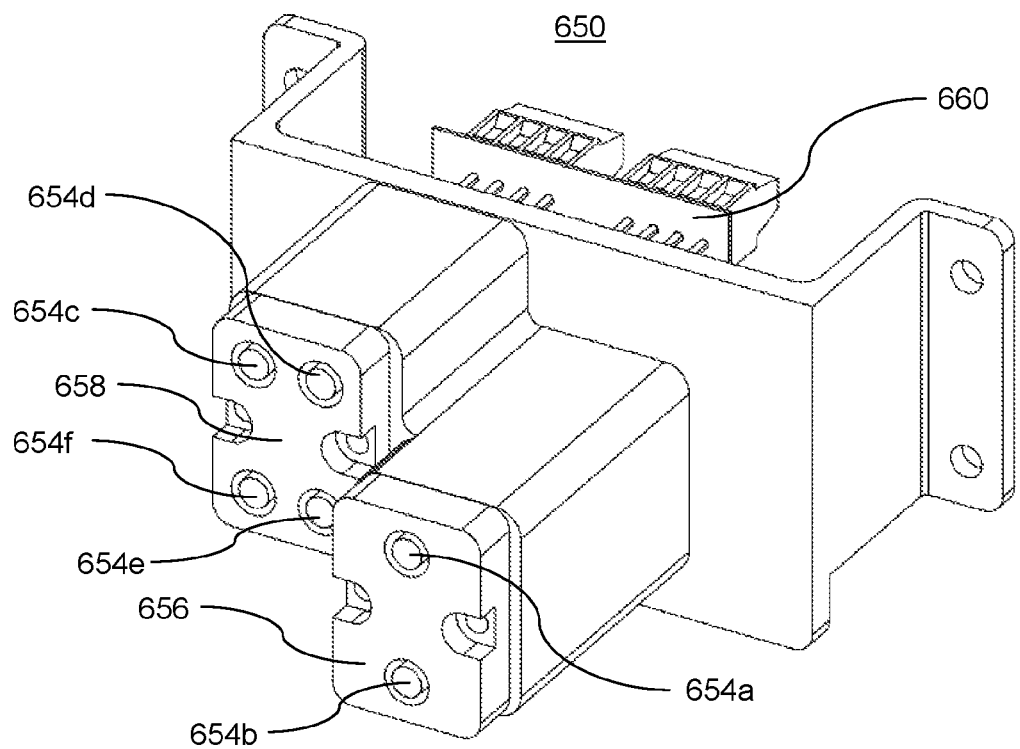
FIG. 8C illustrates a perspective view of an electromagnetic unit carrying electromagnetic elements of the electromagnetic control system of FIG. 8A and FIG. 8B, in accordance with an embodiment of the present disclosure.

Referring to FIG. 8A to FIG. 8C, the electromagnetic control system 650 is configured for performing a mixing process in or as part of the assay process. The electromagnetic control system 650 comprises a set of electromagnetic units 652 for generating magnetic fields within the receptacle 500, or more specifically, within the cuvettes 200 housed in the receptacle 500. The magnetic fields facilitate physical mixing of the assay samples in the cuvettes 200 by causing movement of a magnetic object 202 in each cuvette 200. The movement of the magnetic objects 202 in the cuvettes 200 physically stirs and mixes the assay samples.

The magnetic objects 202 may be made of a neodymium or ferrite material such that it can be moved by effects of the magnetic fields. More specifically, the cores of the magnetic objects 202 are made of the neodymium/ferrite material and the magnetic objects 202 are externally coated with an inert material. This inert material is non-reactive with the assay samples and seeks to prevent contamination of the assay samples which could affect the assay results. The magnetic objects 202 should be small to fit inside the cuvettes 200 with sufficient space to move about for stirring and mixing the assay samples.

Each electromagnetic unit 652 comprises an array of electromagnetic elements 654, and each cuvette 200 is associated with one or more arrays of electromagnetic elements 654. The electromagnetic elements 654 may be or comprise magnetic rods for generating the magnetic fields. FIG. 8C illustrates an example of an electromagnetic unit 652 comprising a first array 656 of two electromagnetic elements 654a,b and a second array 658 of four electromagnetic elements 654c,d,e,f. The electromagnetic unit 652 further comprises a PCB 660 for controlling the magnetic fields generated by the electromagnetic elements 654a-f. The PCB 660 may further comprise or be attached to a layer of silicone thermal for dissipation of heat.

In some embodiments, e.g. for calculation of ACR to diagnose CKD, there are three cuvettes 200 containing the assay samples with the magnetic objects 202. A first cuvette 200b and a second cuvette 200b are preloaded with BCG, and a third cuvette 200a is preloaded with DNBA. The electromagnetic control system 650 comprises two electromagnetic units 652 disposed on opposing sides of the biofluid assay apparatus 30. The two electromagnetic units 652 are facing each other and three cuvettes 200 reside between them. Each of the two electromagnetic units 652 comprises the first array 656 of electromagnetic elements 654a,b and second array 658 of electromagnetic elements 654c-f. The arrangement of the cuvettes 200 with the electromagnetic units 652 may be such that a cuvette 200 is located next or adjacent to one or more electromagnetic units 652, and one or more arrays of electromagnetic elements 654 is targeted towards the cuvette 200. The number of electromagnetic units 652 and electromagnetic elements 654 targeting a cuvette 200 may be dependent on the number of cuvettes 200 residing in the biofluid assay apparatus 30, shape of the cuvettes 200, and/or availability of space for the electromagnetic units 652.

For example and with reference to FIG. 8A, the DNBA-loaded cuvette 200a may be located between the two electromagnetic units 652, specifically between the first arrays 656 of two electromagnetic elements 654a,b each. Referring now to FIG. 8B, one of the BCG-loaded cuvettes 200b may be located adjacent to one electromagnetic unit 652, specifically adjacent to the second array 658 of four electromagnetic elements 654c-f. Similarly, the other BCG-loaded cuvette 200b may be located adjacent to the second array 658 of four electromagnetic elements 654c-f of the other electromagnetic unit 652. As each cuvette 200 is located next to at least one electromagnetic unit 652, the assay samples in all three cuvettes 200 can be mixed at substantially the same time by controlling the magnetic fields with the PCBs 660.

The PCBs 660 may be programmed with or store machine-readable instructions executable for magnetization of the electromagnetic elements 654, e.g. by applying electric currents to the electromagnetic units 652, thereby attracting the magnetic objects 202 towards the electromagnetic elements 654. Accordingly, the motion paths of magnetic objects 202 in the cuvettes 200 can be controlled. More specifically, each electromagnetic element 654 is individually operable for moving a magnetic object 202 along a predefined path within a cuvette 200. Alternatively, the PCBs 660 may be communicatively linked to the central or main PCB of the apparatus 30, such that the electromagnetic units 652 and electromagnetic elements 654 are controlled by the central or main PCB.

Figure 8D:
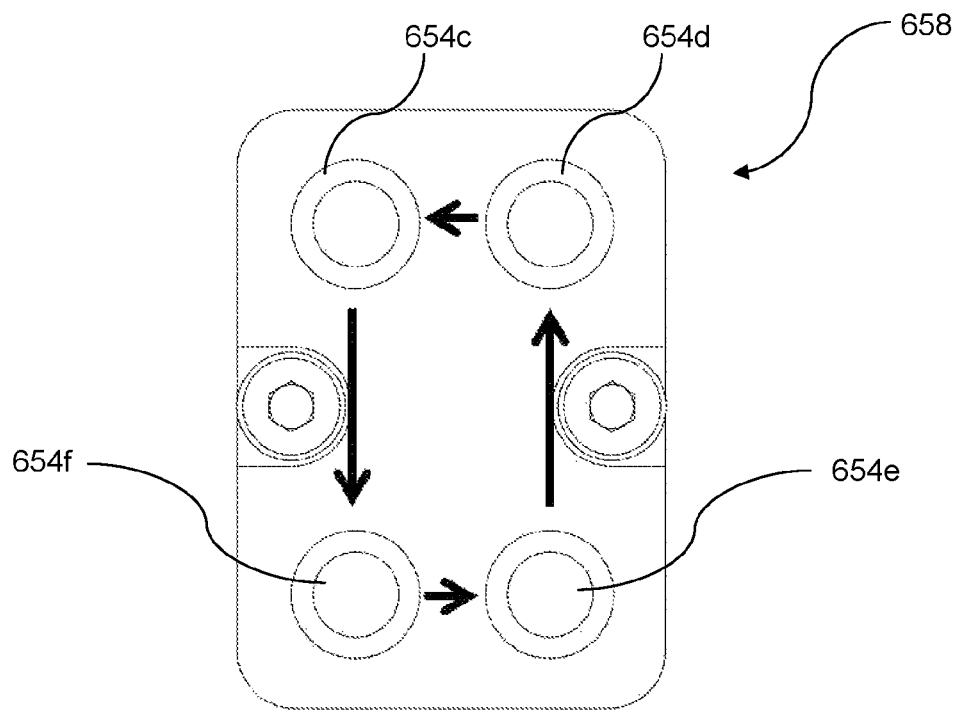
FIG. 8D illustrates a motion path of a magnetic object by the electromagnetic unit of FIG. 8C, in accordance with an embodiment of the present disclosure.
Figure 8E:
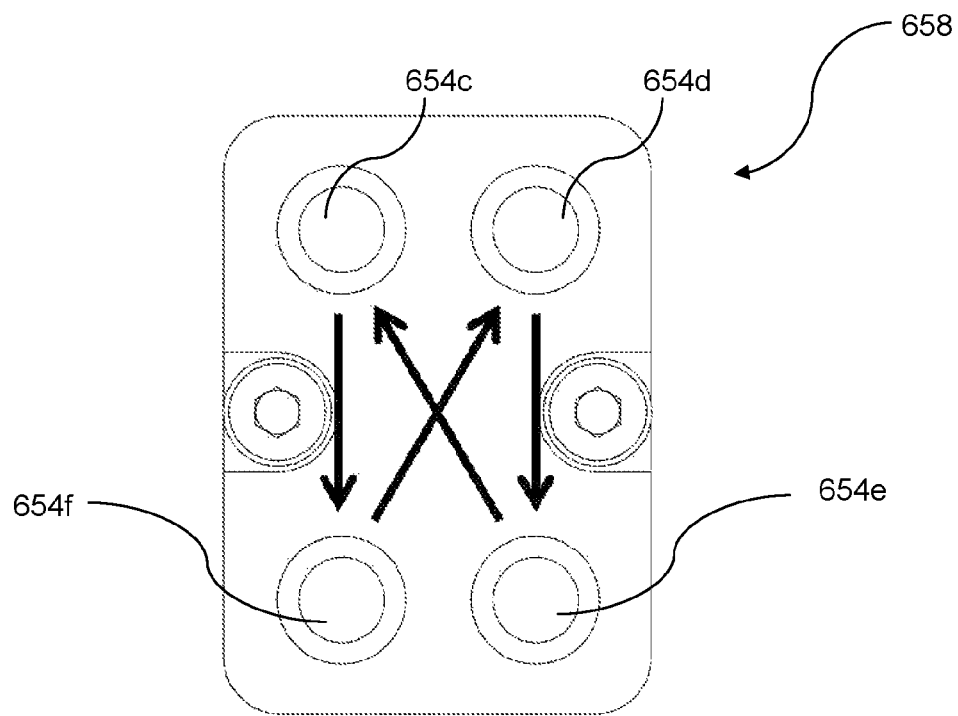
FIG. 8E illustrates an alternative motion path of the magnetic object of FIG. 8D, in accordance with an embodiment of the present disclosure.

In one example relating to the DNBA-loaded cuvette 200a, there are four electromagnetic elements 654a,b (from both of the first arrays 656) for controlling movement of the magnetic object 202. By controlling the sequence, timing, duration, number of loops/cycles of magnetization of each electromagnetic element 654a,b, the magnetic object 202 can be controlled to move in a substantially quadrilateral/circular motion path. Specifically, the motion path resides on a plane that is perpendicular to both of the first arrays 656. In another example relating to one of the BCG-loaded cuvettes 200b, there are four electromagnetic elements 654c-f from one of the second arrays 658 on only one side of the cuvette 200. The magnetic object 202 can similarly be controlled to move in a substantially quadrilateral/circular motion path residing on a plane that is parallel to the second array 658. An example of a quadrilateral motion path is shown in FIG. 8D. Another example of an alternative motion path of the magnetic object 202 is shown in FIG. 8E.

Figure 8F:
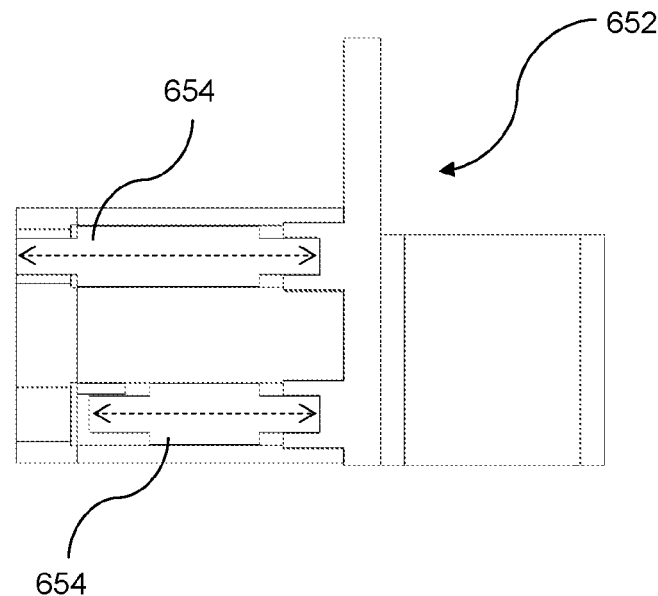
FIG. 8F illustrates the electromagnetic unit of FIG. 8C with different lengths for holding electromagnetic elements, in accordance with an embodiment of the present disclosure.

It would be appreciated that the magnetic object 202 in a cuvette 200 can be controlled to move in different motion paths depending on the orientation of the electromagnetic units 652 facing the cuvette 200 and/or the number electromagnetic elements 654 targeting the cuvette 200. By controlling magnetic fields with the PCBs, the magnetic objects 202 can be moved at desired timings, speed, and direction to physically mix the biofluid samples and reagents together in the assay samples. In addition, the electromagnetic units 652 may be configured to have varying lengths or dimensions for holding the electromagnetic elements 654, as shown in FIG. 8F. This allows for some electromagnetic elements 654 to be nearer the cuvettes 200 than the other electromagnetic elements 654, providing for more variations in controlling the strength of the magnetic fields at different positions along the motion paths.

It would also be appreciated that the magnetic object 202 in a cuvette 200 can be controlled to move in different motion paths depending on the magnetic strength of the electromagnetic units 652 facing the cuvette 200 and/or the distance of each of the electromagnetic elements 654 positioned closer or further away. By controlling magnetic fields with the PCBs 660, the magnetic objects 202 can be moved in an alternating manner in an in-and-out fashion, thereby physically mixing the biofluid samples and reagents together in the assay samples.

Therefore, by operating the electromagnetic control system 650 to generate and apply magnetic fields to the receptacle 500, the assay samples can be physically mixed by the magnetic objects 202 without any contact with an outside component, e.g. a glass stirrer, or by continuous inversion method. Without needing to insert the glass stirrer to mix the assay samples, the biofluid assay apparatus 30 can be used for safely assaying biohazard samples. Additionally, there is minimal to no bubbles formed when mixing. The electromagnetic control system 650 thus provides an automated method for physically mixing the assay samples in the cuvettes 200. Moreover, if there is a restricted time period for mixing the assay samples, the PCBs 660 can be programmed as such to ensure the assay samples are homogenously mixed within the time period. Notably, homogenous mixing or agitation of the assay samples means that there is no remaining or unmixed biofluid sample or reagent in the assay samples.

The electromagnetic control system 650 may be operated before, during, or after the evacuation process. For example, after mixing of the assay samples by operation of the electromagnetic control system 650, there may be remaining air bubbles in the assay samples depending on the type of reagents and/or mixing speed. The air bubbles may affect or compromise measurement of assay results, e.g. by light absorption with the optical system 700. Performing the evacuation process after operation of the electromagnetic control system 650 would substantially de-bubble the assay samples, i.e. substantially remove the air bubbles from the assay samples. Alternatively, the evacuation process may occur simultaneously with operation of the electromagnetic control system 650, such that there is a lower tendency for air bubbles to form in the assay samples during the mixing process. Experimental data indicates that negative vacuum pressure in the range of −55 to −100 kPa, more preferably −70 to −90 kPa, is sufficient to maintain an acceptable vacuum level in the cuvettes 200. A vacuum pump with a maximum degree rating of 25 to 28 Hg would be able to achieve this vacuum level. This vacuum level in the cuvettes 200 may be maintained for the duration of the mixing process, e.g. for 0.5 to 3 minutes or generally less than 3 minutes. Yet alternatively, the evacuation process may be performed before operation of the electromagnetic control system 650. This would create a substantially vacuum environment in the cuvettes 200, which also reduces the tendency for air bubbles to form in the assay samples during the mixing process.

Optical System 700

Figure 9A:
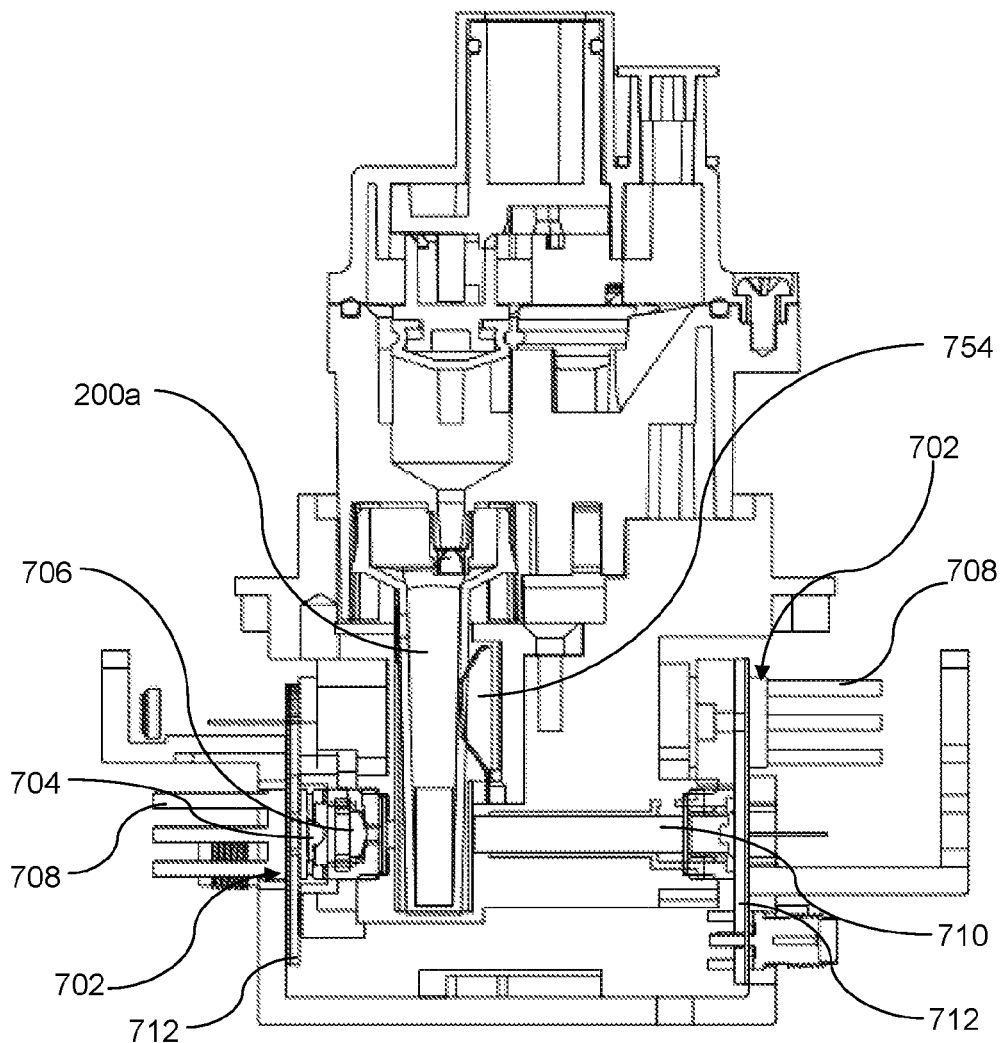
FIG. 9A illustrates a cross-sectional view of an optical system of an apparatus for assaying biofluid, particularly in relation to a DNBA-loaded cuvette, in accordance with an embodiment of the present disclosure.
Figure 9B:
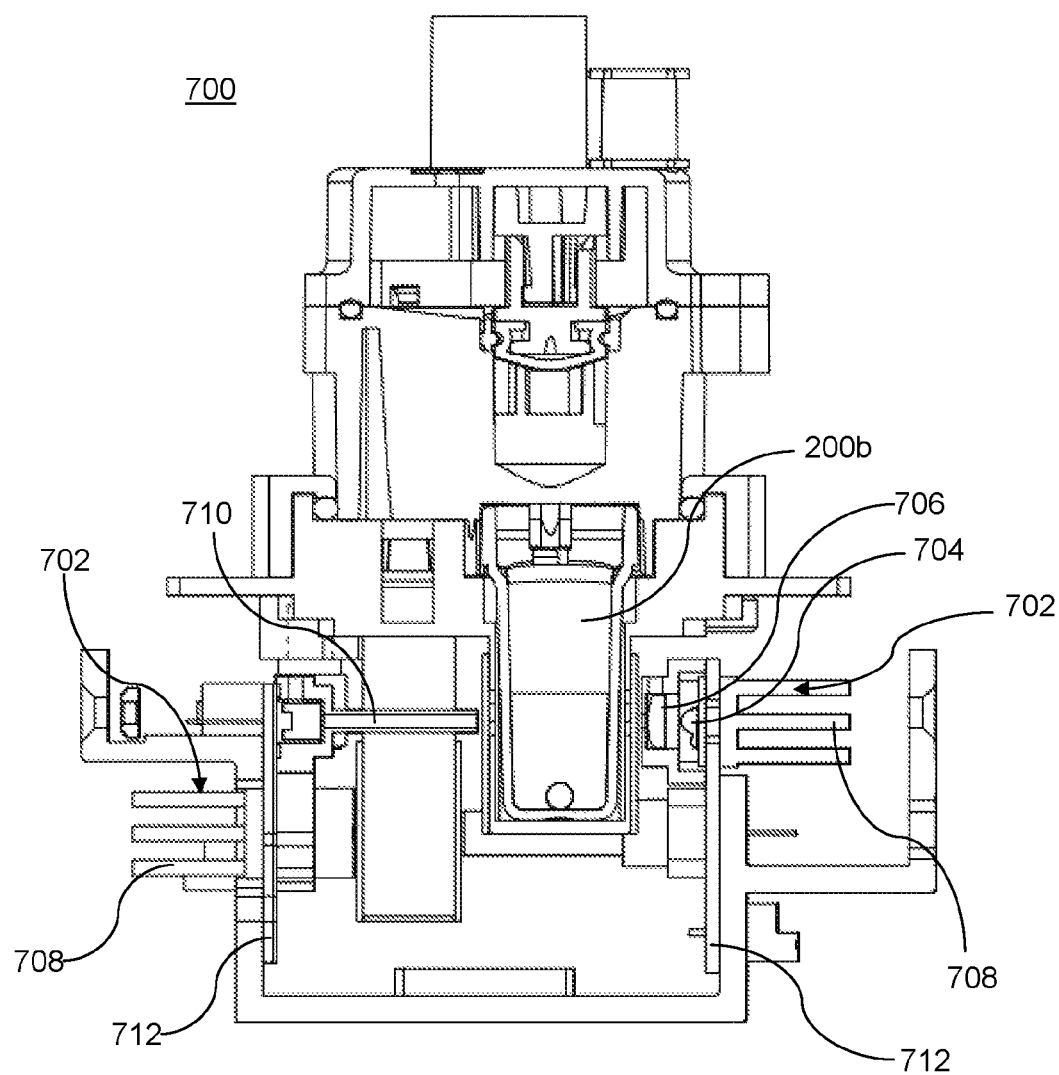
FIG. 9B illustrates another cross-sectional view of the optical system of FIG. 9A, particularly in relation to BCG-loaded cuvettes, in accordance with an embodiment of the present disclosure.

Referring to FIG. 9A and FIG. 9B, the optical system 700 is configured for performing a spectroscopic inspection process in or as part of the assay process. After the assay samples have been mixed, the spectroscopic inspection process analyzes or studies the interaction of the assay samples with electromagnetic radiation, e.g. light. For example, the spectroscopic inspection process is used to determine the presence of albumin in the assay samples comprising reagent BCG and biofluid sample urine, and the presence of creatinine in the assay sample comprising reagent DNBA and biofluid sample urine.

The optical system 700 comprises a set of optical units 702, each optical unit 702 for performing the spectroscopic inspection process on a cuvette 200 containing the respective assay sample. In some embodiments, e.g. for calculation of ACR to diagnose CKD, there are three cuvettes 200 containing the assay samples. Each cuvette 200 is associated or paired with an optical unit 702 such that each optical unit 702 is specifically configured for performing the spectroscopic inspection process on one cuvette 200 only. The assay samples in all three cuvettes 200 can thus be inspected at substantially the same time.

Each optical unit 702 comprises an illumination device 704, e.g. light emitting diode (LED) for emitting light into the cuvette 200. As the light emitted from the illumination device 704 may be divergent, each optical unit 702 comprises one or more optical elements 706 arranged for the collimation/redirection of light, e.g. convergent lens, a combination of convergent and divergent lens, or an array of lens, for collimating the emitted light into the assay sample in the cuvette 200. Alternatively, the optical elements 706 may diverge and then converge the light from the illumination devices 704. The optical elements 706 thus converges the light from the illumination devices 704 towards the assay samples in the cuvettes 200. The emission of light from the illumination devices 704 may release heat also. To mitigate overheating problems which could affect performance or damage the optical system 700, each optical unit 702 comprises a heat sink 708 for absorbing/dissipating heat from the illumination device 704. The heat sink 708 is also used to dissipate heat away to prevent any inaccurate resultant or effect onto the biofluid samples and reagents together in the assay samples.

Each optical unit 702 further comprises a spectroscopy instrument 710, e.g. photodiode or photodetector, for performing spectroscopic measurements on the illuminated assay sample in the respective cuvette 200. Specifically, the spectroscopy instrument 710 is used to measure change in the light absorption of the assay sample. The spectroscopy instrument 710 may be a silicon-based photodiode for detecting and measuring electromagnetic radiation, e.g. light in the 400 to 900 nm wavelength range. In each optical unit 702, the illumination device 704 and the spectroscopy instrument 710 are located on opposite sides of the assay sample, such that the emitted light from the illumination device 704 can pass through the assay sample before being detected and measured by the spectroscopy instrument 710. Further, the optical units 702 are arranged such that the light paths between each pair of illumination device 704 and spectroscopy instrument 710 do not intersect or interfere with one another, allowing the assay samples to be inspected substantially simultaneously.

In each assay sample, the biofluid sample, e.g. urine, reacts with the reagent, e.g. DNBA or BCG, in a colorimetric chemical reaction which causes absorption change. Different coloured light or light of different wavelengths is preconfigured to match the absorption wavelength of the reacted assay sample. Accordingly, the illumination devices 704 may be catered to specific wavelengths required by the assay samples. Alternatively, the illumination devices 704 may be configurable for emitting light of various wavelengths or a range of wavelengths. A graph of absorbance value against time is measured for each assay sample. The albumin or creatinine concentration in the assay sample can then be obtained by utilizing predetermined calibration curves of albumin and creatinine concentrations. After obtaining the concentrations of creatinine and albumin in the urine, the ACR which is a useful parameter for diagnosing CKD can be calculated.

In one example for detecting presence and concentration of creatinine in urine, there is an assay sample in a cuvette 200 comprising DNBA and urine, as shown in FIG. 9A. The illumination device 704 associated with the DNBA-loaded cuvette 200a is configured to emit green light in the 495 to 570 nm wavelength range into the assay sample. Preferably, the green light has a wavelength of around 530 nm. If there is presence of creatinine in the urine, the creatinine would react with DNBA to form a purple-red complex. The rate of formation of the complex is directly proportional to the concentration of creatinine in the urine. The concentration of creatinine can be determined by measuring the change of the absorbance spectra, under effects of the green light, of the complex over a period of time, calculating the rate of the absorbance change of the complex over the period of time, and comparing the calculated rate to a predetermined calibration curve of creatinine concentration.

In another example for detecting presence and concentration of albumin in urine, there is a first assay sample and a second assay sample in two cuvettes 200, each assay sample comprising BCG and urine, as shown in FIG. 9B. The second assay sample is added with another reagent for denaturing the urine and this assay sample is used as a control or reference for the first assay sample to compare against. The illumination devices 704 associated with the BCG-loaded cuvettes 200b are configured to emit red light in the 620 to 750 nm wavelength range into the respective assay samples. Preferably, the red light has a wavelength of around 630 nm. If there is presence of albumin in the urine, the albumin would react with BCG to form a coloured complex. For the second assay sample with the additional reagent for denaturing the urine, the formation of the complex is blocked. Accordingly, the first assay sample results in formation of the complex, while the second assay sample does not form the complex. The colour intensity of the complex is directly proportional to the concentration of albumin in the urine. The concentration of albumin can be determined by measuring the absorbance spectra, under effects of the red light, of the first and second assay samples, calculating the difference between the absorbance spectra of the first and second assay samples, and comparing the calculated difference spectrum to a predetermined calibration curve of albumin concentration.

Although the spectroscopic measurements in the spectroscopic inspection process are described with respect to absorption spectroscopy wherein the assay samples absorb electromagnetic radiation, e.g. light, of a predefined wavelength, other forms of spectroscopic measurements may be performed on the assay samples. For example, other forms of spectroscopic measurements may relate transmission spectroscopy, reflectance spectroscopy, and scattering spectroscopy. Briefly, in transmission spectroscopy, light is transmitted through the assay samples and the transmitted light is compared against light that did not pass through the assay samples. In reflectance spectroscopy, light is emitted to the assay samples and the reflection of the light from the assay samples is analyzed. Scattering spectroscopy is similar to reflectance spectroscopy in that the analysis is performed on the scattering or dispersing of light from the assay samples. In order to perform other forms of spectroscopic measurements, the optical system 700 may comprise additional or alternative components. These may include, but are not limited to, light sources for emitting light of various wavelengths, photo detectors, lens, mirrors, and other known optic/optical components. The different forms of spectroscopic measurements may require different or specific optic/optical components and their arrangement and configuration in the optical system 700 may vary, as would be readily understood by the skilled person.

Additionally, the sealing engagement between the biofluid sample dispensing apparatus 20 and the receptacle 500 of the biofluid assay apparatus 30 prevents misalignment, displacement, and/or vibration so that the spectroscopic measurements performed by the optical system 700 is accurate to minimize noise affected by any further movement.

To assist automation of the spectroscopic measurements, each optical unit 702 further comprises a PCB 712 programmed or stored with machine-readable instructions executable for controlling various components of the optical unit 702. Alternatively, the PCBs 712 may be communicatively linked to the central or main PCB of the apparatus 30, such that the optical units 702 are controlled by the central or main PCB. The PCB 712 may further comprise or be attached to a layer of silicone thermal for dissipation of heat.

In each optical unit 702, the spectroscopy instrument may be configured to perform the spectroscopic measurements on the illuminated assay sample in the cuvette 200 after a predefined duration of time has lapsed since the emission of light from the illumination device 704 into the cuvette 702. Further, the emission of light may occur in response to completion of the mixing process performed by the electromagnetic control system 650, or after a predefined duration of time has lapsed, e.g. 0.5 to 3 minutes or generally less than 3 minutes for completing the mixing process. Accordingly, the mixing process and the spectroscopic inspection process can co-operate together with reduced or minimal manual user intervention. More broadly, the assay process performed on the assay samples can be largely automated.

Temperature Control System 750

Figure 10:
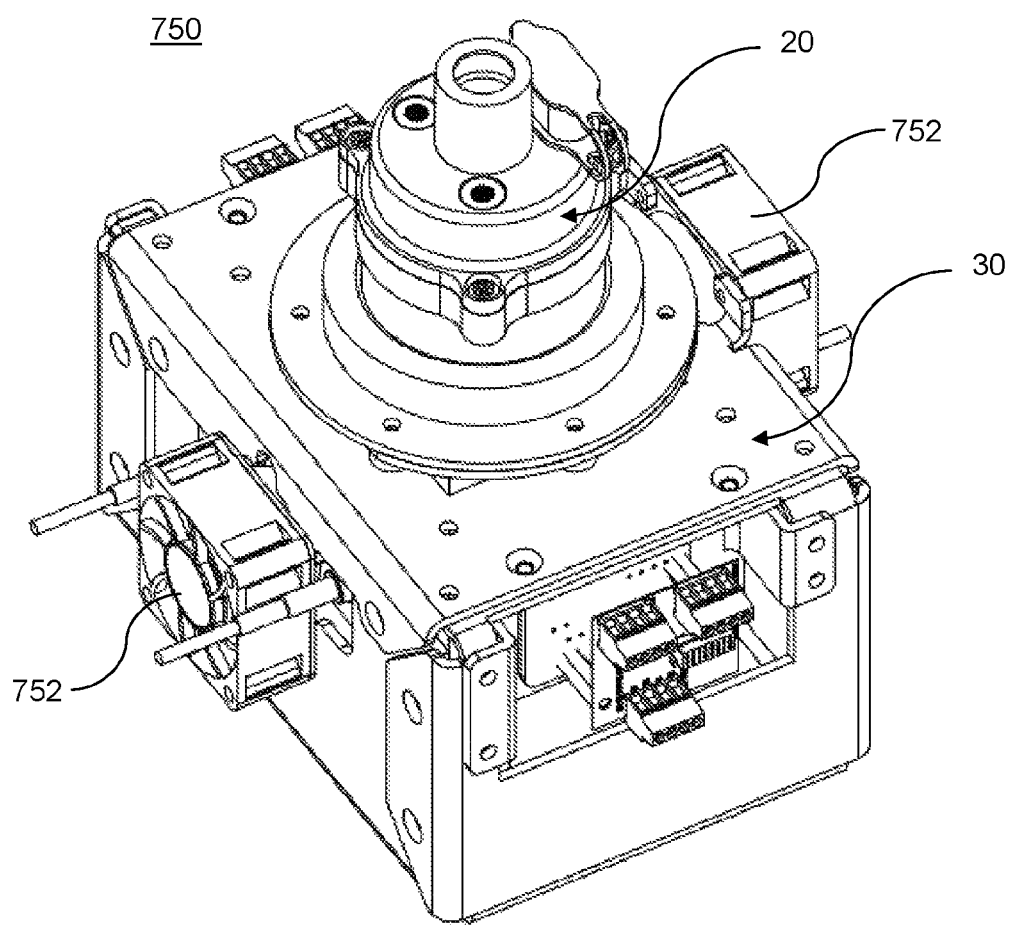
FIG. 10 illustrates a temperature control system of an apparatus for assaying biofluid, in accordance with an embodiment of the present disclosure.

Referring to FIG. 10, the temperature control system 750 is configured for performing a temperature control process in or as part of the assay process. The chemical reactions in the assay samples are usually affected by the environment or ambient temperature. Particularly, a higher ambient temperature may accelerate the rate of reaction, and this may sometimes be unwanted. Controlling the temperature for the chemical reactions can increase the reliability of the assay results, e.g. for calculation of ACR to diagnose CKD. The temperature control process may be performed prior to the dispensation of the biofluid samples into the cuvettes 200 for reaction with the reagents. This would provide a constant environment in each cuvette 200 and ensure that each reaction starts at around the same temperature.

The temperature control system 750 comprises a set of heating and/or cooling elements for maintaining the receptacle 500 or a chamber/space inside the receptacle 500 at a predefined temperature. Specifically, the set of heating/cooling elements are configured for maintaining the cuvettes 200 housed in the receptacle 500 (or a chamber/space in the receptacle 500) at the predefined temperature. The predefined temperature for the reactions of urine with DNBA or BCG may be in the range of 35 to 40° C.

If the ambient temperature is above the predefined temperature, the heating and/or cooling elements, e.g. cooling fans as shown in FIG. 10, may be activated for improving air circulation to dissipate heat from the biofluid assay apparatus 30, thereby adjusting the temperature of the cuvettes 200 towards the predefined temperature. If the ambient temperature is below the predefined temperature, the heating and/or cooling elements, e.g. heaters 754 as shown in FIG. 9A, may be activated for generating heat in the cuvettes 200, thereby adjusting the temperature of the cuvettes 200 towards the predefined temperature. The heaters 754 may be disposed inside the receptacle sockets 504 for emitting heat into the receptacle sockets 504 and consequently heating the cuvettes 200. Alternatively, the heaters may be disposed around the inside of the receptacle sockets 504 such that the heaters 754 are in contact with the cuvettes 200 for direct heating thereof. Yet alternatively, the heaters 754 may be included as components of the electromagnetic units 652.

Preferably, the heating and/or cooling elements 752 may be programmed or configured to be automatically operated in response to deviations from the predefined temperature. Further, the body casing 506 of the biofluid assay apparatus 30 may be made of a heat-conductive material, e.g. sheet metal, which may assist with the homogenization of temperature in the biofluid assay apparatus 30. The biofluid assay apparatus 30 can thus quickly reach and maintain at the predefined temperature as a result of the temperature control process. The temperature control system 750 may include a thermostat that can be configured to provide temperature data within the apparatus 30 for gathering temperature feedback, so as to adopt appropriate approaches for temperature control. It would be appreciated that the temperature feedback and control may be controlled by a PCB of the temperature control system 750, and/or by the central or main PCB of the apparatus 30.

While the biofluid sample dispensing apparatus 20 and the biofluid assay apparatus 30 have been described above as separate apparatuses that are coupleable together, it would be appreciated that the apparatuses 20 and 30 may be combined or assembled together as an integrated system 40 for dispensing and assaying biofluid.

System 40

Figure 11A:
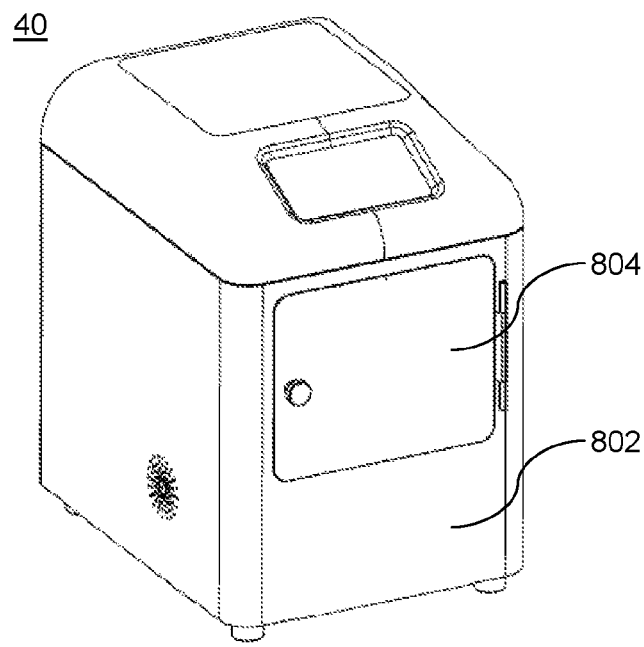
FIG. 11A illustrates an external view of a system for dispensing and assaying biofluid, in accordance with an embodiment of the present disclosure.
Figure 11B:
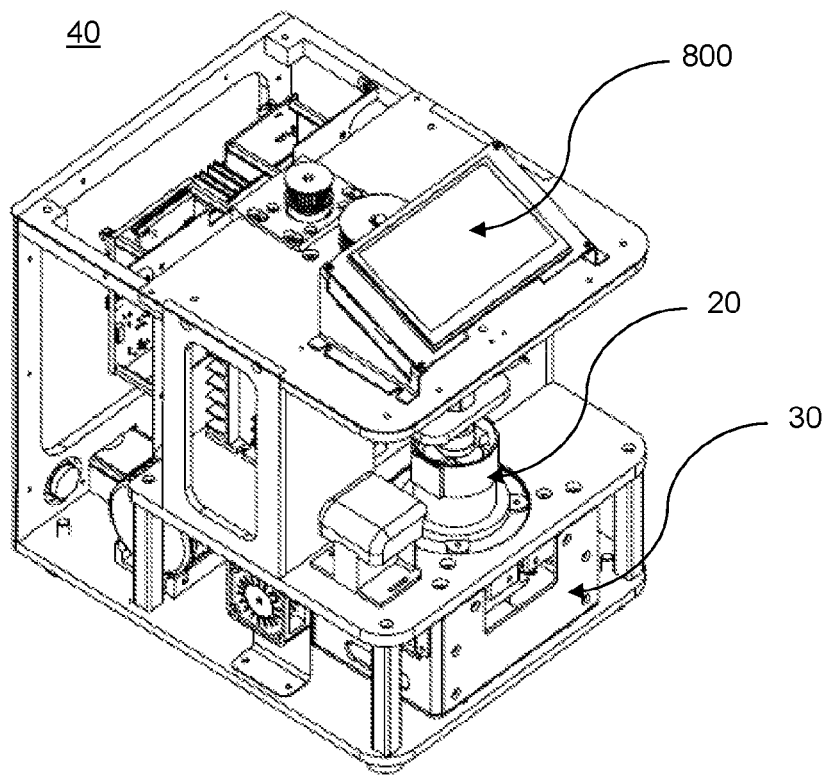
FIG. 11B illustrates an internal view of the system of FIG. 11A, in accordance with an embodiment of the present disclosure.

In representative or exemplary embodiments of the present disclosure, there is a system 40 for dispensing and assaying biofluid as illustrated in FIG. 11A and FIG. 11B. The system 40 comprises a biofluid sample dispensing apparatus 20 and a biofluid assay apparatus 30 as described above. The biofluid sample dispensing apparatus 20 comprises a set of cavities 102, each cavity 102 configured for dispensing a predetermined sample volume of biofluid. The biofluid sample dispensing apparatus 20 further comprises a set of valves 110 for releasably sealing the biofluid samples in the cavities 102, each valve 110 being coupled to a cavity 102. The biofluid sample dispensing apparatus 20 further comprises a set of cuvettes 200 for receiving the biofluid samples through the valves 110, each cuvette 200 being coupled/coupleable to at least one cavity 102 and containing a reagent. The biofluid assay apparatus 30 comprises a receptacle 500 for housing the cuvettes 200, a receptacle sealing element 502 for providing sealing engagement between the receptacle 500 and the biofluid sample dispensing apparatus 20 for sealing the cuvettes 200 within the receptacle 500, and an automated system connected to the receptacle 500 for performing an assay process on an assay sample in each cuvette 200. The biofluid samples are dispensable from the cavities 102 into the cuvettes 200 to combine with the reagent therein, thereby creating the assay samples for the assay process.

The system 40 can provide a low cost, simple, and compact solution for metering, dispensing, and assaying biofluid samples with reagents. Several common and manual processes such as metering and dispensing of the biofluid samples, evacuation process, and mixing process can be at least partially automated by use of the system 40. The automated system for performing the assay process enables non-skilled personnel, e.g. home users, to be able to perform the assay process with greater reliability and repetability. The assay results obtained would be more consistent and less prone to human errors, which may happen in cases whereby colour changes are measured by the human eye.

The system 40 further comprises a computing apparatus 800 for facilitating performance of the assay process. The computing apparatus 800 may include a monitor and a set of input devices for the user, e.g. clinician, to perform and analyze the assay process. For example, the user may operate the computing apparatus 800 as a user interface, to key in the user defined parameters to control the temperature control process for adjusting the desired temperature, program the motion paths of the magnetic objects 202 to ensure homogenous mixing/agitation of the assay samples, and/or analyze assay measurements and results from the spectroscopic inspection process. Alternatively, with all the conditions provided, the user may accordingly adjust the boundary conditions to optimize and gather the results.

The system 40 comprises a body 802 for housing the biofluid sample dispensing apparatus 20 and biofluid assay apparatus 30. The body 802 protects the apparatuses 20 and 30 from damage. The body 802 includes an access door 804 for the user to access and operate the apparatuses 20 and 30. For example, the user may insert the apparatus 20 comprising a cartridge 100 with loaded biofluid samples into the apparatus 30 through the access door 804. The access door 804 may then be closed before commencing the dispensation and performing the assay process.

Figure 12A:
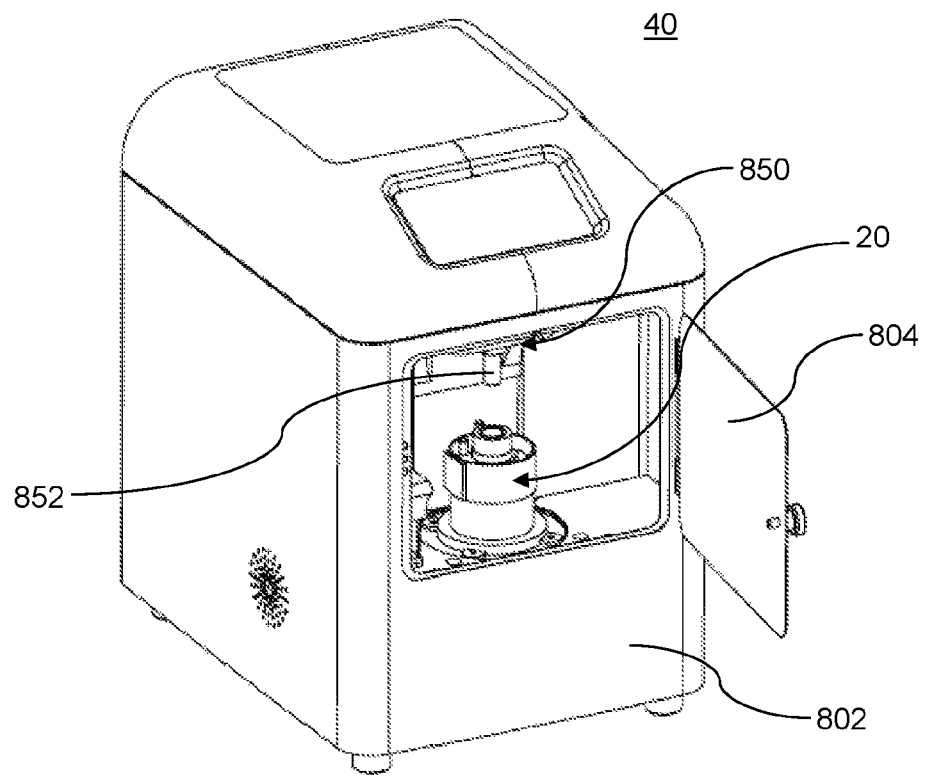
FIG. 12A illustrates a perspective view of a system for dispensing and assaying biofluid, together with a dispensing apparatus in an unactuated state, in accordance with an embodiment of the present disclosure.
Figure 12B:
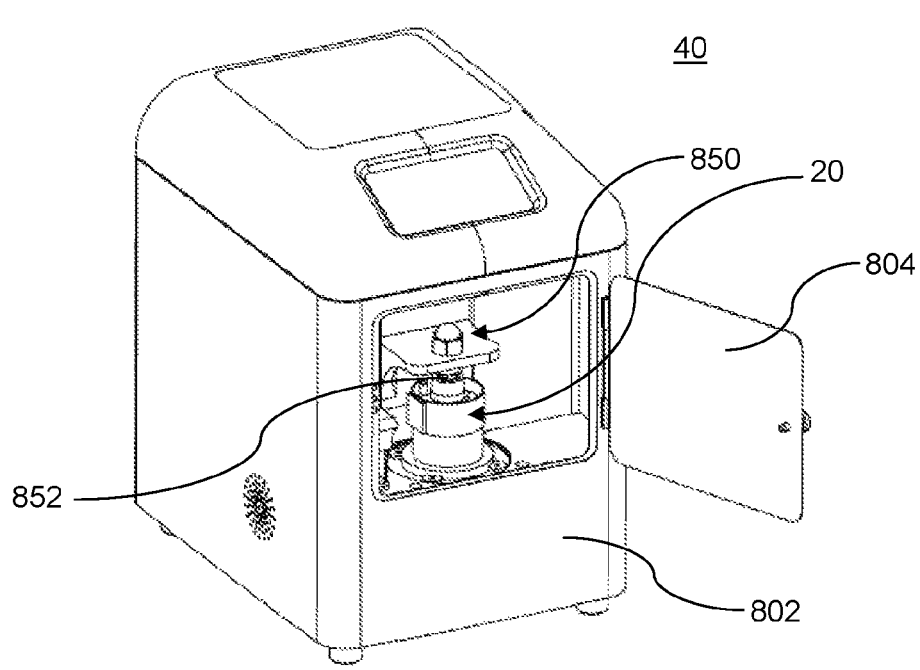
FIG. 12B illustrates another perspective view of the system of FIG. 12A with the dispensing apparatus in an actuated state, in accordance with an embodiment of the present disclosure.

Referring to FIG. 12A and FIG. 12B, in order to automate dispensation of the biofluid samples, the system 40 comprises a dispenser apparatus 850 for effecting dispensation of the biofluid samples from the cavities 102 into the cuvettes 200 through the valves 110. The dispenser apparatus 850 comprises an actuator 852, e.g. a lead screw, for displacing a set of pistons 402 of the biofluid sample dispensing apparatus 20. Displacement of the pistons 402 exerts positive pressure on the biofluid samples, thereby opening the valves 110 and dispensing the biofluid samples therethrough. FIG. 12A shows the dispenser apparatus 850 with the actuator 852 in a default or unactuated state, and FIG. 12B shows the actuator 852 in the displaced or actuated state.

The dispenser apparatus 850 further comprises an actuating mechanism which may be controlled by an electric motor, e.g. stepper motor, or manually operated. The stepper motor may operate together with gears for guiding movement of the actuator 852, as well as with limit switches for stopping the actuator 852 at the intended position. The dispenser apparatus 850 may also be integrated with a timer or timing device so that precise time control of the actuating mechanism can be achieved for dispensing the biofluid samples. The dispenser apparatus 850 may also be controlled by the computing apparatus 800 and configurable for adjusting the speed of the actuator 852, thereby controlling the rate of dispensation of the biofluid samples. The start of the chemical reaction between the biofluid samples and the reagents can thus be controlled, such that the chemical reaction in each cuvette 200 can begin at substantially the same time. The reaction times or durations are important in order to obtain reliable, accurate, and consistent assay results. If the reaction times are measured manually, human errors are more likely to occur, such as due to human reaction delays.

During dispensation, the actuator 852 may be displaced at a low speed ranging from 0.4 to 0.8 mm/s. Each piston 402 would consequently be displaced at the same speed to dispense the biofluid samples into the cuvettes 200. At this low speed, the coefficient of variation between the amounts of biofluid samples dispensed into the cuvettes 200 can be controlled to within 2% or less. This would result in improved reliability and consistency in the subsequent assay results as the amount of biofluid samples in all the cuvettes 200 is substantially the same.

In the foregoing detailed description, embodiments of the present disclosure in relation to an apparatus and a system for dispensing and/or assaying at least one biofluid are described with reference to the provided figures. The description of the various embodiments herein is not intended to call out or be limited only to specific or particular representations of the present disclosure, but merely to illustrate non-limiting examples of the present disclosure. For example, although embodiments of the present disclosure are described in relation to urinalysis, it would be readily apparent to the skilled person that the apparatus and system described herein may alternatively be used for other applications and/or diagnosis of other diseases.

The present disclosure serves to address at least one of the mentioned problems and issues associated with the prior art. Although only some embodiments of the present disclosure are disclosed herein, it will be apparent to a person having ordinary skill in the art in view of this disclosure that a variety of changes and/or modifications can be made to the disclosed embodiments without departing from the scope of the present disclosure. Therefore, the scope of the disclosure as well as the scope of the following claims is not limited to embodiments described herein.

The invention claimed is:

1. A system for dispensing and assaying biofluid, the system comprising:
   a biofluid sample dispensing apparatus comprising:
   a set of reservoirs;
   a set of cavities for dispensing a set of biofluid samples, each cavity of the set of cavities residing within a respective reservoir of the set of reservoirs and configured for dispensing a respective biofluid sample of the set of biofluid samples, each biofluid sample of the set of biofluid samples having a predetermined sample volume of biofluid;

a set of valves for releasably sealing the set of biofluid samples in the set of cavities, each valve of the set of valves being coupled to a respective cavity of the set of cavities for releasably sealing a respective biofluid sample of the set of biofluid samples;

a piston assembly for dispensing the set of biofluid samples from the set of cavities through the set of valves; and a set of cuvettes for receiving the set of biofluid samples dispensed by the piston assembly from the set of cavities through the set of valves, the set of cuvettes being coupled to the set of cavities and containing one or more reagents; and a biofluid assay apparatus comprising:

a receptacle for removably housing the set of cuvettes;

a receptacle sealing element disposed around the receptacle for providing sealing engagement between the receptacle and the biofluid sample dispensing apparatus for sealing the set of cuvettes within the receptacle; and an automated assay system connected to the receptacle for performing a set of assay processes on a set of assay samples in the set of cuvettes.

2. The system according to claim 1, wherein the piston assembly comprises a set of pistons, and wherein the system further comprises an actuator for displacing the set of pistons of the piston assembly to dispense the set of biofluid samples from the set of cavities into the set of cuvettes through the set of valves.

3. The system according to claim 1, wherein the automated assay system comprises an electromagnetic control system for performing a mixing process on the set of assay samples in the set of cuvettes.

4. The system according to claim 3, wherein the electromagnetic control system comprises a set of electromagnetic units for generating magnetic fields within the set of cuvettes to facilitate physical mixing of the set of assay samples in the set of cuvettes.

5. The system according to claim 4, wherein each cuvette of the set of cuvettes comprises a magnetic object, and wherein the magnetic objects in the set of cuvettes are moveable by the magnetic fields for physically mixing the set of assay samples in the set of cuvettes.

6. The system according to claim 5, wherein each electromagnetic unit of the set of electromagnetic units comprises an array of electromagnetic elements.

7. The system according to claim 6, wherein each cuvette of the set of cuvettes is paired with a respective electromagnetic unit of the set of electromagnetic units, and wherein for each respective cuvette of the set of cuvettes, each electromagnetic element of the array of electromagnetic elements of the paired respective electromagnetic unit of the set of electromagnetic units is individually operable for moving the magnetic object in the respective cuvette of the set of cuvettes along a predefined path within the respective cuvette of the set of cuvettes.

8. The system according to claim 2, wherein displacement of the set of pistons exerts positive pressure on the set of biofluid samples, thereby opening the set of valves and dispensing the set of biofluid samples through the set of valves.

9. The system according to claim 8, wherein displacement of the set of pistons is configured to actuate in a stepwise manner to dispense the set of biofluid samples at staggering times.

10. The system according to claim 1, wherein the set of biofluid samples is dispensable into the set of cuvettes to combine with the one or more reagents contained in the set of cuvettes, thereby creating the set of assay samples for the set of assay processes.

* * * * *